(12) United States Patent
Buchstaller et al.

(10) Patent No.: US 7,875,614 B2
(45) Date of Patent: Jan. 25, 2011

(54) PHTHALAZINONES

(75) Inventors: Hans-Peter Buchstaller, Griesheim (DE); Dirk Finsinger, Darmstadt (DE); Kai Schiemann, Seeheim-Jugenheim (DE); Ulrich Emde, Darmstadt (DE); Frank Zenke, Darmstadt (DE); Christiane Amendt, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 689 days.

(21) Appl. No.: 11/886,294

(22) PCT Filed: Feb. 21, 2006

(86) PCT No.: PCT/EP2006/001525

§ 371 (c)(1),
(2), (4) Date: Sep. 14, 2007

(87) PCT Pub. No.: WO2006/097176

PCT Pub. Date: Sep. 21, 2006

(65) Prior Publication Data

US 2008/0194569 A1 Aug. 14, 2008

(30) Foreign Application Priority Data

Mar. 15, 2005 (DE) .................. 10 2005 011 822

(51) Int. Cl.
| | |
|---|---|
| C07D 237/32 | (2006.01) |
| A61K 31/502 | (2006.01) |
| A61P 35/00 | (2006.01) |
| A61P 9/10 | (2006.01) |
| A61P 29/00 | (2006.01) |
| A61P 19/02 | (2006.01) |
| A61P 25/28 | (2006.01) |

(52) U.S. Cl. .................................... 514/248
(58) Field of Classification Search ................. 544/237; 514/248

See application file for complete search history.

(56) References Cited

U.S. PATENT DOCUMENTS 3,864,343 A 2/1975 Inoue et al.

6,180,629 B1 1/2001 Wang et al.
7,714,151 B2 * 5/2010 Kelly et al. ............. 549/404

FOREIGN PATENT DOCUMENTS

| DE | 22 38 566 | 2/1973 |
|---|---|---|
| WO | WO 03/014090 A | 2/2003 |

OTHER PUBLICATIONS

Vaughan, et al., The Preparation of Some Phthalazines and Related Substances, Journal of the American Chemical Society American Chemical Society, vol. 68, pp. 1314-1316 (1946).
Bernard, et al., A New and Efficient Synthesis of Phthalazin-1(2H)-ones, Synthesis, pp. 317-320 (1998).
Al-Awadhi, et al., New Synthetic Approaches to Condensed Pyridazinones: Aklylpyridazinyl Carbonitriles . . . , Tetrahedron, vol. 51, pp. 12745-12762 (1995).
Elnagdi, et al., Studies on Alkyl Heterocyclic Aromatic Compounds: New Routes for the Synthesis of Polyazanaphthalenes, Verlag der Zeitschrift für Naturforschung, pp. 683-689 (1998).

* cited by examiner

*Primary Examiner*—James O Wilson
*Assistant Examiner*—Cecilia M Jaisle
(74) *Attorney, Agent, or Firm*—Perkins Coie LLP

(57) ABSTRACT

Compounds of the formula I, in which R, $R^1$, $R^2$, $R^3$, $R^4$, $R^5$, $R^6$, $R^7$, $R^8$, $Z^1$, $Z^2$, $Z^3$ and $Y^1$ have the meanings indicated in claim 1, can be employed, inter alia, for the treatment of tumours

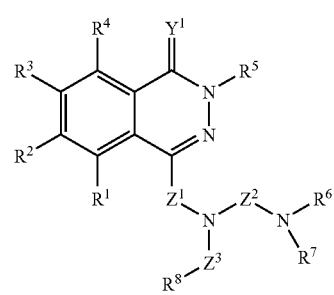

I

13 Claims, No Drawings

PHTHALAZINONES

The present application is a National Phase of International Application No. PCT/EP2006/001525 filed Feb. 21, 2006 and claims priority to German Patent Application No. 10 2005 011 822.4 filed Mar. 15, 2005. The contents of both applications are expressly incorporated herein by reference in their entireties.

The invention had the object of finding novel compounds having valuable properties, in particular those which can be used for the preparation of medicaments.

The present invention relates to compounds of the formula I and to the use thereof for the treatment and prophylaxis of diseases in which the inhibition, regulation and/or modulation of mitotic motor proteins, in particular the mitotic motor protein Eg5, plays a role, furthermore to pharmaceutical compositions which comprise these compounds.

In detail, the present invention relates to compounds of the formula I which preferably inhibit, regulate and/or modulate one or more mitotic motor proteins, to compositions which comprise these compounds, and to methods for the use thereof for the treatment of diseases and complaints such as angiogenesis, cancer, tumour formation, growth and propagation, arteriosclerosis, ocular diseases, choroidal neovascularisation and diabetic retinopathy, inflammatory diseases, arthritis, neurodegeneration, restenosis, wound healing or transplant rejection. In particular, the compounds according to the invention are suitable for the therapy or prophylaxis of cancer diseases.

During mitosis, various kinesins regulate the formation and dynamics of the spindle apparatus, which is responsible for correct and coordinated alignment and separation of the chromosomes. It has been observed that specific inhibition of a mitotic motor protein—Eg5—results in collapse of the spindle fibres. The result of this is that the chromosomes can no longer be distributed correctly over the daughter cells. This results in mitotic arrest and can thus cause cell death. Upregulation of the motor protein Eg5 has been described, for example, in tissue from breast, lung and colon tumours. Since Eg5 takes on a mitosis-specific function, it is principally rapidly dividing cells and not fully differentiated cells that are affected by Eg5 inhibition. In addition, Eg5 regulates exclusively the movement of mitotic microtubuli (spindle apparatus) and not that of the cytoskeleton. This is crucial for the side-effect profile of the compounds according to the invention since, for example, neuropathies, as observed in the case of Taxol, do not occur or only do so to a weakened extent. The inhibition of Eg5 by the compounds according to the invention is therefore a relevant therapy concept for the treatment of malignant tumours.

In general, all solid and non-solid tumours can be treated with the compounds of the formula I, such as, for example, monocytic leukaemia, brain, urogenital, lymphatic system, stomach, laryngeal and lung carcinoma, including lung adenocarcinoma and small-cell lung carcinoma. Further examples include prostate, pancreatic and breast carcinoma.

Surprisingly, it has been found that the compounds according to the invention effect specific inhibition of mitotic motor proteins, in particular Eg5. The compounds according to the invention preferably exhibit an advantageous biological activity which can easily be detected in the assays described herein, for example. In such assays, the compounds according to the invention preferably exhibit and cause an inhibiting effect, which is usually documented by $IC_{50}$ values in a suitable range, preferably in the micromolar range and more preferably in the nanomolar range.

As discussed herein, effects of the compound according to the invention are relevant to various diseases. Accordingly, the compounds according to the invention are useful in the prophylaxis and/or treatment of diseases which are influenced by inhibition of one or more mitotic motor proteins, in particular Eg5.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases, and also to a method for the treatment of the said diseases comprising the administration of one or more compounds according to the invention to a patient in need of such an administration.

It can be shown that the compounds according to the invention have an advantageous effect in a xenotransplant tumour model.

The host or patient can belong to any mammal species, for example a primate species, particularly humans; rodents, including mice, rats and hamsters; rabbits; horses, cattle, dogs, cats, etc. Animal models are of interest for experimental investigations, providing a model for the treatment of a human disease.

The susceptibility of a certain cell to treatment with the compounds according to the invention can be determined by testing in vitro. Typically, a culture of the cell is combined with a compound according to the invention at various concentrations for a periodine which is sufficient to enable the active ingredients to induce cell death or inhibit migration, usually between approximately one hour and one week. For testing in vitro, cultivated cells from a biopsy sample can be used. The viable cells remaining after the treatment are then counted.

The dose varies depending on the specific compound used, the specific disease, the patient status, etc. Typically, a therapeutic dose is sufficient considerably to reduce the undesired cell population in the target tissue, while the viability of the patient is maintained. The treatment is generally continued until a considerable reduction has occurred, for example at least about a 50% reduction in the cell burden, and can be continued until essentially no undesired cells are detected in the body.

The invention relates to compounds of the formula I

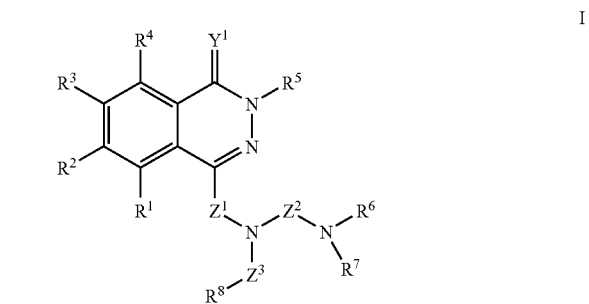

in which
$R^1$, $R^2$, $R^3$ and $R^4$, independently of one another, denote H, A, Ar, Het, $OR^a$, $SR^a$, OAr, SAr, $N(R^a)_2$, $NR^aAr$, Hal, $NO_2$, CN, $(CH_2)_mCOOR^a$, $(CH_2)_mCOOAr$, $(CH_2)_mCON(R^a)_2$, $(CH_2)_mCONHAr$, $COR^a$, COAr, $S(O)_mA$, $S(O)_mAr$, NHCOA, NHCOAr, $NHSO_2A$, $NHSO_2Ar$ or $SO_2N(R^a)_2$, $R^a$ denotes H, A, Ar, Het, aralkyl or heteroaralkyl, $R^5$, $R^8$, independently of one another, denote H, A, Ar, Het, aralkyl or heteroaralkyl, and $R^6$, $R^7$, independently of one another, denote H or A, or, together with the N atom to which they are bonded, form a saturated or unsaturated 5-, 6- or 7-membered heterocycle, which may optionally contain 1, 2 or 3 further heteroatoms selected from N, S and O, $Y^1$ denotes O, S or $NR^1$, $Z^1$, $Z^2$, $Z^3$, independently of one another, denote $(CR^9R^{10})_n$ or $(CR^9R^{10})_p$—(C=$Y^2$)—$(CR^{11}R^{12})_q$, A denotes alkyl or cycloalkyl, Ar denotes aryl or heteroaryl, Het denotes heteroaryl or heterocyclyl, Hal denotes F, Cl, Br or I, $Y^2$ denotes O, S or $NR^2$, $R^9$, $R^{10}$, $R^{11}$, $R^{12}$, independently of one another, denote H, A, OA, Ar, Het, aralkyl or heteroaralkyl, m denotes 0, 1, 2 or 3, n denotes 1, 2, 3 or 4, and p, q, independently of one another, denote 0, 1, 2 or 3, and pharmaceutically usable derivatives, solvates, tautomers, salts and stereoisomers thereof, including mixtures thereof in all ratios.

The invention also relates to the optically active forms, the enantiomers, the racemates, the diastereomers and the hydrates and solvates of these compounds. Solvates of the compounds are taken to mean adductions of inert solvent molecules onto the compounds of the formula I which form owing to their mutual attractive force. Solvate are, for example, mono- or dihydrates or alcoholates.

Pharmaceutically usable derivatives are taken to mean, for example, the salts of the compounds according to the invention and also so-called prodrug compounds or prodrug derivatives. Suitable prodrug compounds or prodrug derivatives and processes for the preparation thereof are known to the person skilled in the art.

Prodrug compounds or prodrug derivatives are preferably taken to mean compounds of the formula I which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995).

Similar compounds are described, for example, in Tetrahedron Lett. 1988, 29, 5855-5858, Tetrahedron Lett. 2003, 44, 217-219, J. Org. Chem. 1997, 62, 4880-4882, J. Org. Chem. 1999, 64, 6462-6467, Chem. Lett. 1995, 423-424, J. Org. Chem. 2000, 65, 5009-5013, Chem. Lett. 2003, 32, 222-223, US2003149069A1, but are not mentioned in connection with cancer treatments and/or do not contain the features that are essential to the invention.

The expression "effective amount" denotes the amount of a medicament or of a pharmaceutical active ingredient which causes in a tissue, system, animal or human a biological or medical response which is sought or desired, for example, by a researcher or physician. In addition, the expression "therapeutically effective amount" denotes an amount which causes at least one of the following effects in a human or another mammal (in comparison with a subject who has not received this amount):

improvement in the healing treatment, healing, prevention or elimination of a disease, syndrome, condition, complaint, disorder or side-effects or also the reduction in the progress of a disease, complaint or disorder. The expression "therapeutically effective amount" also encompasses the amounts which are effective for increasing or enhancing normal physiological function.

For the purposes of the present invention, the term "herein" preferably means "in the description and/or claims" and in particular "above and/or below in the description and/or claims". Thus, for example, the expression "as described herein" preferably has the meaning "as described in the description and/or claims" and in particular the meaning "as described above and/or below in the description and/or claims".

The invention also relates to the use of mixtures of the compounds of the formula I, for example mixtures of two diastereomers, for example mixtures of two diastereomers in the ratio of about 1:1, 1:2, 1:3, 1:4, 1:5, 1:10, 1:100 or about 1:1000.

These are particularly preferably mixtures of stereoisomeric compounds.

The invention relates to the compounds of the formula I and salts thereof and to a process for the preparation of compounds of the formula I according to the patent claims and pharmaceutically usable derivatives, salts, solvates and stereoisomers thereof, characterised in that a) a compound of the formula II

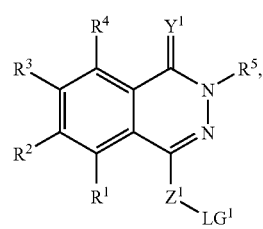

II in which $R^1$, $R^2$, $R^3$, $R^4$, $R^5$, $Y^3$ and $Z^1$ have the meanings indicated herein, and $LG^1$ stands for a leaving group, is reacted with a compound of the formula III

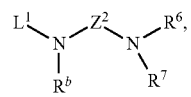

III in which $R^6$, $R^7$ and $Z^2$ have the meanings indicated herein, $L^1$ stands for H or a metal atom, $R^b$ stands either for $L^2$ or for $Z^3$-$R^8$, in which $L^2$ stands for H or a metal atom and $Z^3$ and $R^8$ have the meaning indicated herein, and, if $R^b$ stands for $L^2$, the product of the formula

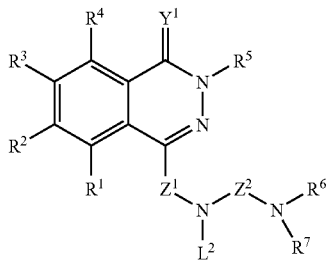

IV obtained in reaction step a) is
b) reacted with a compound of the formula V

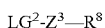 LG²-Z³—R⁸    V, in which
$Z^3$ and $R^8$ have the meaning indicated herein, and
$LG^2$ stands for a leaving group, and optionally
c) the resultant compound of the formula I is isolated and/or treated with an acid or a base in order to convert it into one of its salts.

Leaving groups $LG^1$ and $LG^2$ which are suitable for the above process are known to the person skilled in the art, for example from standard works, such as Houben-Weyl, Methoden der organischen Chemie [Methods of Organic Chemistry], Georg-Thieme-Verlag, Stuttgart.

$LG^1$ preferably stands for a leaving group selected from Hal, in particular Cl, Br or I, and $OSO_2R^e$, in which $R^e$ is preferably selected from
A, in particular alkyl, such as methyl and trifluoromethyl, and
Ar, in particular phenyl or substituted phenyl.
$LG^1$ particularly preferably stands for $OSO_2CH_3$.
$LG^2$ preferably stands for a leaving group selected from Hal, in particular Cl, Br or I, and $OSO_2R^e$, in which $R^e$ is preferably selected from
A, in particular alkyl, such as methyl and trifluoromethyl, and
Ar, in particular phenyl or substituted phenyl.
$LG^2$ particularly preferably stands for Hal, particularly preferably Cl, Br or I, and in particular for Cl.
$L^1$ and $L^2$ preferably stand, independently of one another, for H or a metal atom, for example for an alkali metal atom, such as Na or K, and particularly preferably for H.

It is furthermore possible to convert a compound of the formula I into another compound of the formula I by converting one or more radical(s), for example one or more radicals selected from $R^1$, $R^2$, $R^3$, $R^4$, $R^5$, $R^5$, $R^6$, $R^7$ and $R^8$, into one or more other radicals $R^1$, $R^2$, $R^3$, $R^4$, $R^5$, $R^5$, $R^6$, $R^7$ and $R^8$(i.e., for example, converting a radical $R^1$ into another radical $R^1$ or converting a radical $R^5$ into another radical $R^5$), for example by reducing nitro groups into amino groups, for example by hydrogenation on Raney nickel or Pd/carbon in an inert solvent, such as methanol or ethanol, and/or converting an ester group into a carboxyl group and/or converting an amino group into an alkylated amine by reductive amination and/or esterifying carboxyl groups by reaction with alcohols.

Furthermore, free amino groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

If desired, a functionally modified amino and/or hydroxyl group in a compound of the formula I can be liberated by solvolysis or hydrogenolysis by conventional methods. This can be carried out, for example, using NaOH or KOH in water, water/THF or water/dioxane at temperatures between 0 and 100°.

The process according to the invention is preferably carried out under reaction conditions which are known and suitable for the said reactions or can be derived in a simple manner from analogous reactions by the person skilled in the art. Use can also be made here of variants known per se which are not mentioned here in greater detail.

The starting materials for the process according to the invention are either commercially available or can be prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for these reactions. Use can also be made here of variants known per se which are not mentioned here in greater detail.

If desired, the starting materials can also be formed in situ by not isolating them from the reaction mixture, but instead immediately converting them further into the compounds according to the invention.

Any mixtures of diastereomers and enantiomers of the compounds of the formula I that are obtained by the process described herein are preferably separated by chromatography or crystallisation.

If desired, the bases and acids of the formula I obtained by the process described herein are converted into their salts.

Above and below, the radicals $R^1$, $R^2$, $R^3$, $R^4$, $R^a$, $R^5$, $R^6$, $R^7$, $R^8$, $R^9$, $R^{10}$, $R^{11}$, $R^{12}$, $Y^1$, $Y^2$, $Z^1$, $Z^2$, $Z^3$, A, Het, Ar, m, n, p and q have the meanings indicated for the formula I, unless expressly indicated otherwise. If individual radicals occur more than once within a compound, the radicals adopt the meanings indicated independently of one another.

Preferred compounds of the formula I are compounds of the formula I'

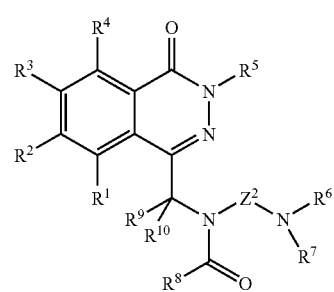

I' in which
$R^1$, $R^2$, $R^3$, $R^4$, $R^5$, $R^6$, $R^7$, $R^8$, $R^9$, $R^{10}$ and $Z^2$ are as defined herein,
$R^9$, $R^{10}$, independently of one another, are selected from H, A, OA, Ar, Het, aralkyl and heteroaralkyl, particularly preferably from H, A, Ar and aralkyl and in particular from H and A, and pharmaceutically usable derivatives, solvates, tautomers, salts and stereoisomers thereof, including mixtures thereof in all ratios.

For the purposes of the invention, alkyl is preferably unbranched (linear) or branched, has 1, 2, 3, 4, 5, 6, 7, 8, 9 or 10 C atoms and may be substituted. Substituted alkyl is preferably an alkyl radical as described in this section which has 1-7, preferably 1-5 and particularly preferably 1-3 substituents, which are preferably selected from Hal, in particular Cl and F, OH, O-alkyl, $NH_2$ and $N(alkyl)_2$, in which alkyl is as described above and is preferably unsubstituted alkyl as described above. Substituted alkyl particularly preferably denotes an alkyl radical as described above in which 1-7 H atoms have been replaced by F and/or chlorine, for example a perchlorinated or perfluorinated alkyl radical. Fluorine- and/or chlorine-substituted alkyl radicals of this type preferably have 1, 2, 3, 4 or 5 C atoms. Preferred fluorine- and/or chlorine-substituted alkyl radicals are perfluorinated alkyl radicals, in particular trifluoromethyl radicals. Unsubstituted or substituted alkyl particularly preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further particularly preferably trifluoromethyl. Alkyl very particularly preferably denotes an alkyl radical having 1, 2, 3, 4, 5 or 6 C atoms, which may be chlorinated and/or fluorinated as described above and is, in particular, selected from methyl, ethyl, propyl, isopropyl, butyl, isobutyl, sec-butyl, tert-butyl, pentyl, hexyl, trifluoromethyl, pentafluoroethyl and 1,1,1-trifluoroethyl.

For the purposes of the invention, cycloalkyl is preferably selected from substituted or unsubstituted cyclopropyl, cyclobutyl, cyclopentyl, cyclohexyl or cycloheptyl. Substituted cycloalkyl is preferably a cycloalkyl radical as described above which has 1-7, preferably 1-5 and particularly preferably 1-3 substituents, which are preferably selected from Hal, in particular Cl and F, OH, O-alkyl, $NH_2$ and $N(alkyl)_2$, in which alkyl is as described above and is preferably unsubstituted alkyl as described above.

For the purposes of this invention, alkylene is preferably an unbranched or branched divalent hydrocarbon radical having 1-10 C atoms, preferably 1-4 C atoms, which may optionally have 1-7, preferably 1-5 and particularly preferably 1-3 substituents, which are preferably selected from Hal, in particular Cl and F, OH, O-alkyl, $NH_2$ and $N(alkyl)_2$, in which alkyl is as described above and is preferably unsubstituted alkyl as described above. Unsubstituted alkylene preferably stands for methylene, ethylene, n-propylene, iso-propylene or n-butylene and in particular for methylene or ethylene.

For the purposes of the invention, aryl is preferably a substituted or unsubstituted benzene ring, for example a phenyl radical, or a system of benzene rings, such as, for example, anthracene, phenanthrene or naphthalene ring systems or radicals. Substituted aryl is preferably an aryl radical as described above which has 1-7, preferably 1-5 and particularly preferably 1-3 substituents, which are preferably selected from Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, $—CH_2—COOH$ or $—OCH_2—COOH$ and in particular from Hal, in particular Cl and F, OH, O-alkyl, $NH_2$ and $N(alkyl)_2$, in which alkyl is as described above and is preferably unsubstituted alkyl as described above.

Aryl therefore particularly preferably denotes phenyl, naphthyl or biphenyl, each of which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, $—CH_2—COOH$ or $—OCH_2—COOH$.

Aryl very particularly preferably denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-nitrophenyl, o-, m- or p-aminophenyl, o-, m- or p-(N-methylamino)-phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

For the purposes of the invention, heteroaryl is preferably a substituted or unsubstituted monocyclic 5- to 7-membered aromatic ring or an unsubstituted or substituted fused ring system comprising two or three monocyclic 5- to 7-membered rings of this type, where the ring or rings contain(s) one or more heteroatoms, preferably selected from N, S and O. A heteroaryl radical preferably contains 1 to 4 heteroatoms as described above and in particular 1 to 4 nitrogen atoms. Examples of heteroaryl radicals are furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted derivatives thereof, preferably derivatives thereof which are mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, $—CH_2—COOH$ or $—OCH_2—COOH$.

Heteroaryl preferably denotes a mono- or bicyclic aromatic heterocycle having one or more N, O and/or S atoms which is unsubstituted or mono-, di- or trisubstituted by Hal, A, $NO_2$, NHA, $NA_2$, OA, COOA or CN.

Heteroaryl particularly preferably denotes a monocyclic saturated or aromatic heterocycle having one N, S or O atom, which may be unsubstituted or mono-, di- or trisubstituted by Hal, A, NHA, $NA_2$, $NO_2$, COOA or benzyl.

Irrespective of further substitutions, unsubstituted heteroaryl denotes, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3, 4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

For the purposes of the invention, aralkyl is preferably an aryl radical as defined above bonded to an alkylene radical as defined above. Aralkyl may be substituted or preferably unsubstituted. Examples of preferred unsubstituted arylalkyl radicals are benzyl, phenethyl, phenylpropyl and phenylbutyl and in particular benzyl and phenethyl. Substituted arylalkyl is preferably an arylalkyl radical as described above which has 1-7, preferably 1-5 and particularly preferably 1-3 substituents, which are preferably selected from Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH and particularly preferably from Hal, in particular Cl and F, OH, O-alkyl, $NH_2$ and $N(alkyl)_2$, in which alkyl is as described above and is preferably unsubstituted alkyl as described above.

For the purposes of the invention, heteroaralkyl is preferably aralkyl as defined above in which one or more C atoms, preferably 1 to 4 C atoms, have been substituted by heteroatoms, preferably selected from N, S and O and in particular from N and S. Heteroaralkyl is particularly preferably a heteroaryl radical as defined above bonded to an alkylene radical as defined above. Heteroaralkyl may be substituted or preferably unsubstituted. Examples of preferred unsubstituted heteroarylalkyl radicals are pyridyl-2-ylmethyl, pyridyl-3-ylmethyl, pyridyl-4-ylmethyl, pyridyl-2-ylethyl, pyridyl-3-ylethyl and pyridyl-4-ylethyl.

For the purposes of the invention, heterocyclyl is preferably an unsaturated or preferably saturated cyclic radical, which preferably has 1 to 6 C atoms and 1 to 4 heteroatoms, preferably selected from N, S and O. Heterocyclyl is preferably a 5-, 6- or 7-membered ring as described above which is unsubstituted or substituted by 1 to 5 and in particular 1 to 3 substituents, where the substituents are preferably selected from Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH, —$OCH_2$—COOH, =O, =S and =N—$R^a$ and in particular from Hal, in particular Cl and F, OH, O-alkyl, $NH_2$, $N(alkyl)_2$, =O and =S. Heterocyclyl is particularly preferably selected from 1-piperidyl, 4-piperidyl, 1-methylpiperidin-4-yl, 1-piperazyl, 1-(4-methyl)piperazyl, 4-methylpiperazin-1-ylamine, 1-(4-(2-hydroxyethyl))piperazyl, 4-morpholinyl, 1-pyrrolidinyl, 2-pyrrolidinyl, 3-pyrrolidinyl, 1-pyrazolidinyl, 1-(2-methyl)pyrazolidinyl, 1-imidazolidinyl or 1-(3-methyl)imidazolidinyl, thiophen-2-yl, thiophen-3-yl, 2-oxazolyl, 4-oxazolyl, 5-oxazolyl, 2-thiazolyl, 4-thiazolyl and 5-thiazolyl, where of the above-mentioned radicals, the saturated radicals are particularly preferred. Particular preference is likewise given to the above-mentioned radicals, in particular the above-mentioned saturated radicals, which have 1, 2 or 3, preferably one or two, substituents selected from A, =O, =S, =N—$R^a$ and Hal. Heterocyclyl is very particularly preferably a saturated radical as defined above which is either unsubstituted or mono- or disubstituted by A or =O.

A denotes alkyl, preferably as described above, and is particularly preferably unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. A also denotes cycloalkyl. Cycloalkyl preferably denotes cyclopropyl, cyclobutyl, cyclopentyl, cyclohexyl or cycloheptyl, but in particular cyclopentyl.

Ar preferably stands for aryl radicals and heteroaryl radicals as described herein and in particular for aryl radicals as described herein.

Het preferably stands for heteroaryl radicals and heterocyclyl radicals as described herein and in particular for heterocyclyl radicals as described herein.

$R^1$, $R^2$, $R^3$ and $R^4$ are preferably, in each case independently of one another, selected from H, A, $CF_3$, $OCF_3$, $OR^a$, SA, $S(O)_2A$, $S(O)A$, $CH_2CN$, COOA, CONHA, Hal, SCF, CN and Het, preferably also from H, Cl, Br, F, t-butyl, —CH($CH_3$)$CH_2CH_3$, isopropyl, ethyl and methyl. $R^1$, $R^2$, $R^3$ and $R^4$ are particularly preferably, in each case independently of one another, selected from H, t-butyl, isopropyl, ethyl, $CF_3$, methyl, Br, Cl, F, $SCF_3$, CH($CH_3$)$CH_2CH_3$, n-propyl, $OCH_3$, $SCH_3$, n-butyl, $CH_2CN$ and Het. In particular, $R^1$, $R^2$, $R^3$ and $R^4$ are, in each case independently of one another, selected from H, Cl, Br, F, t-butyl, isopropyl, ethyl or $CF_3$.

At least one of the radicals $R^1$, $R^2$, $R^3$ and $R^4$ is preferably different from H. One, two or three of the radicals $R^1$, $R^2$, $R^3$ and $R^4$ are particularly preferably different from H.

At least one of the radicals $R^1$, $R^2$, $R^3$ and $R^4$, particularly preferably one, two or three of the radicals $R^1$, $R^2$, $R^3$ and $R^4$, is therefore preferably, in each case independently of one another, selected from A, Ar, Het, OR , SR , OAr, SAr, $N(R^a)_2$, $NR^aAr$, Hal, $NO_2$, CN, $(CH_2)_mCOOR^a$, $(CH_2)_mCOOAr$, $(CH_2)_mCON(R^a)_2$, $(CH_2)_mCONHAr$, $COR^a$, COAr, $S(O)_mA$, $S(O)_mAr$, NHCOA, NHCOAr, $NHSO_2A$, $NHSO_2Ar$ and $SO_2N(R^a)_2$.

At least one of the radicals $R^1$, $R^2$, $R^3$ and $R^4$, particularly preferably one, two or three of the radicals $R^1$, $R^2$, $R^3$ and $R^4$, is therefore particularly preferably, in each case independently of one another, selected from A, $CF_3$, $OCF_3$, $OR^a$, SA, $S(O)_2A$, $S(O)A$, $CH_2CN$, COOA, CONHA, Hal, SCF, CN and Het, preferably also from H, Cl, Br, F, t-butyl, —CH($CH_3$)$CH_2CH_3$, isopropyl, ethyl and methyl, very particularly preferably selected from t-butyl, isopropyl, ethyl, $CF_3$, methyl, Br, Cl, F, $SCF_3$, CH($CH_3$)$CH_2CH_3$, n-propyl, $OCH_3$, $SCH_3$, n-butyl, $CH_2CN$ and Het, and in particular selected from Cl, Br, F, t-butyl, iso-propyl, ethyl or $CF_3$.

$R^1$ and/or $R^4$ preferably stand for H.

$R^2$ and/or $R^3$ preferably stand for a radical which is different from H, preferably selected from the above-mentioned radicals which are different from H.

$R^2$ and/or $R^3$ preferably stand for Hal, A or OA, in particular Cl, cyclopropyl or $OCH_3$.

In particularly preferred compounds of the formula I, one of the radicals $R^2$ and $R^3$ has the meaning H and the other radical has the meaning Cl.

$R^a$ preferably denotes H, A, Ar, Het, aralkyl or heteroaralkyl, particularly preferably H, A, Ar, Het or aralkyl I, very particularly preferably H, A, Ar or Het and in particular H, A or Ar. If $R^a$ stands for A, Ar, Het, aralkyl or heteroaralkyl, the said radicals may also be substituted. $R^a$ then generally has 1 to 5 and preferably 1 to 3 substituents, preferably selected from Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH and in particular from Hal, in particular Cl and F, OH, O-alkyl, $NH_2$ and $N(alkyl)_2$, in which alkyl is as described above and is preferably unsubstituted alkyl as described above.

$R^5$ preferably denotes H, A, Ar, Het, aralkyl or heteroaralkyl, particularly preferably A, Ar, Het, aralkyl or heteroaralkyl, very particularly preferably A, Ar, aralkyl or heteroaralkyl and in particular aralkyl or heteroaralkyl. In particular, $R^5$ denotes benzyl, phenethyl or phenylpropyl, or substituted derivatives thereof. If $R^5$ stands for substituted benzyl, phenethyl or phenylpropyl, it has 1 to 5 and preferably 1 to 3 substituents, preferably selected from Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH and in particular from Hal, in particular Cl and F, OH, O-alkyl, $NH_2$ and $N(alkyl)_2$, in which alkyl is as described above and is preferably unsubstituted alkyl as described above.

$R^8$ preferably denotes H, A, Ar, Het, aralkyl or heteroaralkyl, particularly preferably A, Ar, Het, aralkyl or heteroaralkyl, very particularly preferably A, Ar, aralkyl or heteroaralkyl and in particular A or Ar. If $R^8$ stands for Ar, Ar is preferably unsubstituted or substituted phenyl. If $R^8$ stands for substituted phenyl, it has 1 to 5 and preferably 1 to 3 substituents, preferably selected from Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH and in particular from Hal, in particular Cl and F, OH, O-alkyl, $NH_2$ and $N(alkyl)_2$, in which alkyl is as described above and is preferably unsubstituted alkyl as described above.

$R^6$ preferably denotes H or A, particularly preferably A. If $R^6$ stands for A, A is preferably substituted or unsubstituted alkyl having 1 to 6 C atoms.

$R^7$ preferably denotes H or A, particularly preferably A. If $R^7$ stands for A, A is preferably substituted or unsubstituted alkyl having 1 to 6 C atoms.

Alternatively, $R^6$ and $R^7$, together with the N atom to which they are bonded, stand for a saturated or unsaturated 5-, 6- or 7-membered heterocycle, preferably form a saturated or unsaturated 5- or 6-membered heterocycle, which may optionally contain 1, 2 or 3 further heteroatoms, preferably 1 or 2 further heteroatoms, which are preferably selected from N, S and O and in particular from N and O. In this embodiment, $NR^6R^7$ preferably stands for 1-piperidyl, 1-piperazyl, 1-(4-methyl)piperazyl, 4-methylpiperazin-1-ylamine, 4-morpholinyl, 1-pyrrolidinyl, 1-pyrazolidinyl, 1-(2-methyl)pyrazolidinyl, 1-imidazolidinyl or 1-(3-methyl)imidazolidinyl, 4-pyridyl, oxazolyl, thiazolyl, quinolinyl, iso-quinolinyl, 2- or 4-pyridazyl, 2-, 4- or 5-pyrimidyl, 2- or 3-pyrazinyl.

$Y^1$ preferably stands for O or S and in particular for O.

$Y^2$ preferably stands for O or S and in particular for O.

$Z^1$ preferably stands for $(CR^9R^{10})_n$ or $(CR^9R^{10})_p$—$(C=Y^2)$—$(CR^{11}R^{12})_q$, in which n preferably stands for 1, 2 or 3, particularly preferably 1 or 2, in particular for 1, in which p preferably stands for 0, 1 or 2, particularly preferably 0 or 1 and in particular for 0, and in which q preferably stands for 0, 1 or 2, particularly preferably 0 or 1 and in particular for 0. In $(CR^9R^{10})_n$, $R^9$ and $R^{10}$, independently of one another, are preferably selected from H, A, OA, Ar, Het, aralkyl and heteroaralkyl, particularly preferably from H, A, Ar and aralkyl and in particular from H and A. In $(CR^9R^{10})_p$—$(C=Y^2)$—$(CR^{11}R^{12})_q$, $R^9$, $R^{10}$; $R^{11}$ and $R^{12}$, independently of one another, are preferably selected from H, A, OA, Ar, Het, aralkyl and heteroaralkyl, particularly preferably from H, A, Ar and aralkyl and in particular from H and A.

In $Z^1$, $(CR^9R^{10})_n$ is preferably selected from $CR^9R^{10}$, CHA, CAA and $CH_2$. In $Z^1$, $(CR^9R^{10})_p$—$(C=Y^2)$—$(CR^{11}R^{12})_q$ is preferably selected from $CR^9R^{10}$—$(C=Y^2)$, $(C=Y^2)$—$CR^{11}R^{12}$ and $C=Y^2$, and in particular from $CR^9R^{10}$—$(C=O)$, $(C=O)$—$CR^{11}R^{12}$ and $C=O$.

$Z^1$ is particularly preferably selected from $CR^9R^{10}$, CHA, CAA and $CH_2$.

$Z^2$ preferably stands for $(CR^9R^{10})_n$ or $(CR^9R^{10})_p$—$(C=Y^2)$—$(CR^{11}R^{12})_q$, in which n preferably stands for 1, 2, 3 or 4, particularly preferably 1, 2 or 3 and in particular for 2 or 3, in which p preferably stands for 0, 1 or 2 and particularly preferably for 0 or 1, and in which q preferably stands for 0, 1 or 2 and particularly preferably for 0 or 1. In $(CR^9R^{10})_n$, $R^9$ and $R^{10}$, independently of one another, are preferably selected from H, A, OA, Ar, Het, aralkyl and heteroaralkyl, particularly preferably from H, A, Ar and aralkyl and in particular from H and A. In $(CR^9R^{10})_p$—$(C=Y^2)$—$(CR^{11}R^{12})_q$, $R^9$, $R^{10}$; $R^{11}$ and $R^{12}$, independently of one another, are preferably selected from H, A, OA, Ar, Het, aralkyl and heteroaralkyl, particularly preferably from H, A, Ar and aralkyl and in particular from H and A.

In $Z^2$, $(CR^9R^{10})_n$ is preferably selected from $CR^9R^{10}$, $(CR^9R^{10})_2$, $(CR^9R^{10})_3$ and $(CR^9R^{11})_4$, in which $R^9$ and $R^{10}$ are as defined above/below and are preferably selected, in each case independently of one another, from H and A. In $Z^2$, $(CR^9R^{10})_n$ is particularly preferably selected from $CH_2$, $(CH_2)_2$, $(CH_2)_3$ and $(CH_2)_4$. In $Z^2$, $(CR^9R^{10})_p$—$(C=Y^2)$—$(CR^{11}R^{12})_q$ is preferably selected from $CR^9R^{10}$—$(C=Y^2)$—$CR^{11}R^{12}$, $CR^9R^{10}$—$(C=Y^2)$, $(C=Y^2)$—$CR^{11}R^{12}$ and $C=Y^2$, and in particular from $CR^9R^{10}$—$(C=O)$, $(C=O)$—$CR^{11}R^{12}$ and $C=O$.

$Z^2$ is particularly preferably selected from $CR^9R^{10}$, $(CR^9R^{10})_2$, $(CR^9R^{10})_3$ and $(CR^9R^{10})_4$, in which $R^9$ and $R^{10}$ are as defined above/below and are preferably selected, in each case independently of one another, from H and A and in particular from $CH_2$, $(CH_2)_2$, $(CH_2)_3$ and $(CH_2)_4$.

$Z^3$ preferably stands for $(CR^9R^{10})_n$ or $(CR^9R^{10})_p$—$(C=Y^2)$—$(CR^{11}R^{12})_q$, in which n preferably stands for 1, 2 or 3, particularly preferably 1 or 2, in particular for 1, in which p preferably stands for 0, 1 or 2, particularly preferably 0 or 1 and in particular for 0, and in which q preferably stands for 0, 1 or 2, particularly preferably 0 or 1 and in particular for 0. In $(CR^9R^{10})_n$, $R^9$ and $R^{10}$ are preferably selected, independently of one another, from H, A, OA, Ar, Het, aralkyl and heteroaralkyl, particularly preferably from H, A, Ar and aralkyl and in particular from H and A. In $(CR^9R^{10})_p$—$(C=Y^2)$—$(CR^{11}R^{12})_q$, $R^9$, $R^{10}$; $R^{11}$ and $R^{12}$ are preferably selected, independently of one another, from H, A, OA, Ar, Het, aralkyl and heteroaralkyl, particularly preferably from H, A, Ar and aralkyl and in particular from H and A.

In $Z^3$, $(CR^9R^{10})_n$ is preferably selected from $CR^9R^{10}$, CHA, CAA and $CH_2$. In $Z^3$, $(CR^9R^{10})_p$—$(C=Y^2)$—$(CR^{11}R^{12})_q$ is preferably selected from $CR^9R^{10}$—$(C=Y^2)$, $(C=Y^2)$—$CR^{11}R^{12}$ and $C=Y^2$, and in particular from $CR^9R^{10}$—$(C=O)$, $(C=O)$—$CR^{11}R^{12}$ and $C=O$.

$Z^3$ is particularly preferably selected from $C=Y^2$, $C=O$ and $C=S$.

$R^8$—$Z^3$ particularly preferably stands for substituted or preferably unsubstituted benzoyl. If $R^8$—$Z^3$ stands for substituted benzoyl, it has 1 to 5 and preferably 1 to 3 substituents, preferably selected from Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH and particularly preferably from Hal, in particular Cl and F, OH, O-alkyl, $NH_2$ and $N(alkyl)_2$, in which alkyl is as described above and is preferably unsubstituted alkyl as described above.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and may therefore occur in various stereoisomeric forms. The formula I encompasses all these forms.

Particularly preferred compounds of the formula I are the compounds of the sub-formulae IA to IL:

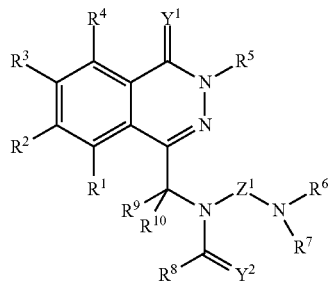
IA

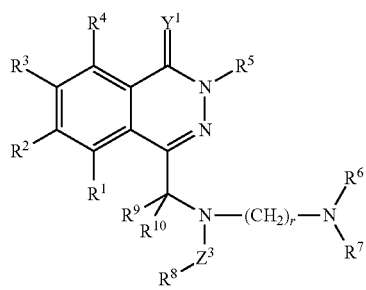
IB

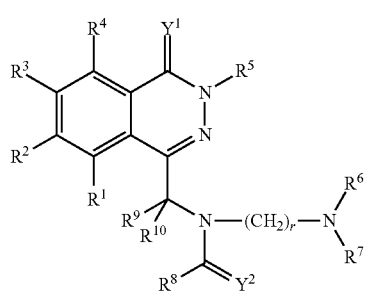
IC

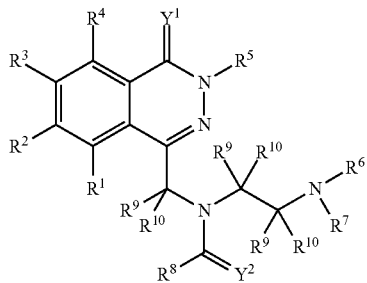
ID

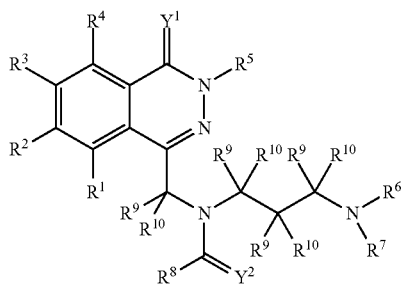
IE

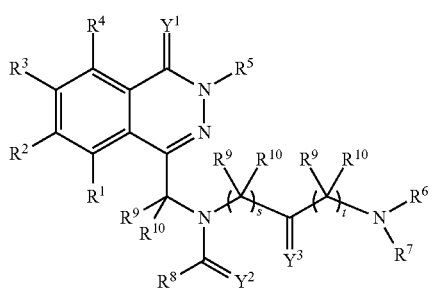
IF

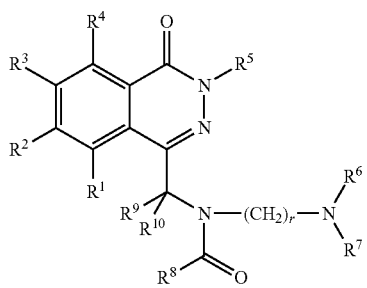
IG

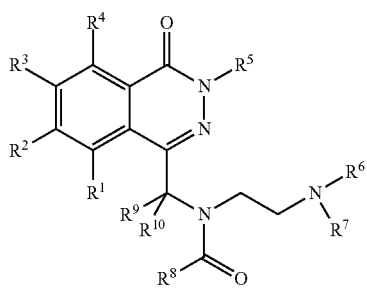
IH

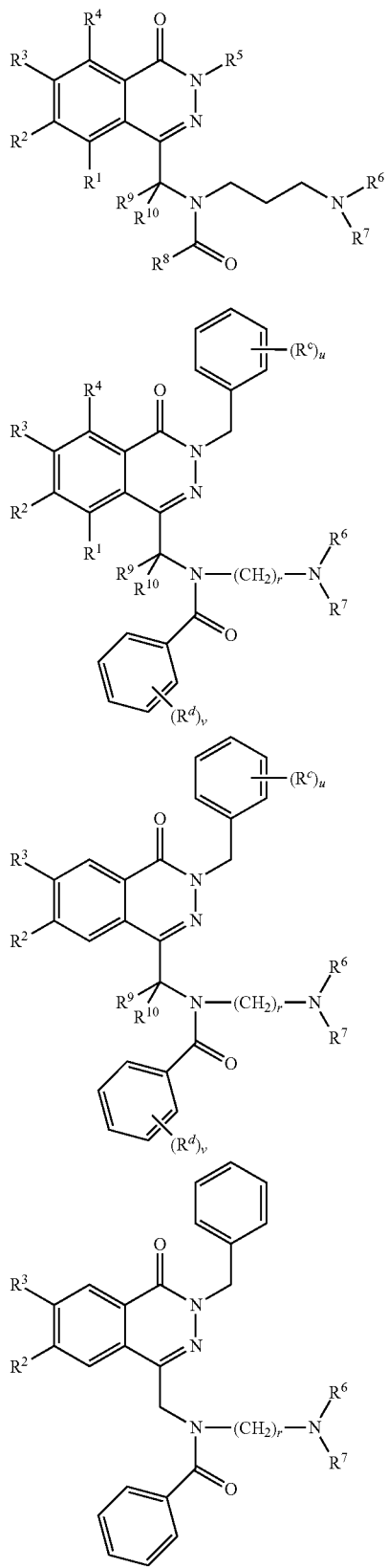

which
R$^1$, R$^2$, R$^3$, R$^4$, R$^5$, R$^6$, R$^7$, R$^8$, R$^9$, R$^{10}$, Y$^1$, Y$^2$, Z$^1$ and Z$^3$ have the meanings indicated herein, r stands for 1, 2, 3 or 4, preferably for 1, 2 or 3 and in particular for 2 or 3, s and t, independently of one another, stand for 0, 1 or 2 and in particular for 0 or 1, Y$^3$ stands for O, S or NR$^a$ and in particular for O or S, R$^c$ and R$^d$, independently of one another, are selected from the meanings indicated for R$^1$ to R$^4$, and u and v, independently of one another, stand for 0, 1, 2 or 3 and in particular for 0, 1 or 2.

Further particularly preferred compounds of the formula I are the compounds of the sub-formulae IM to IP:

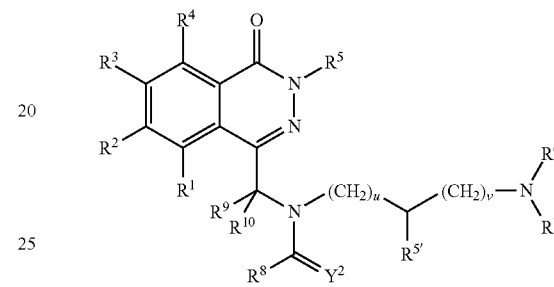

IM

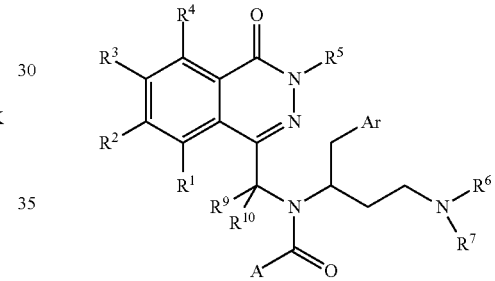

IN

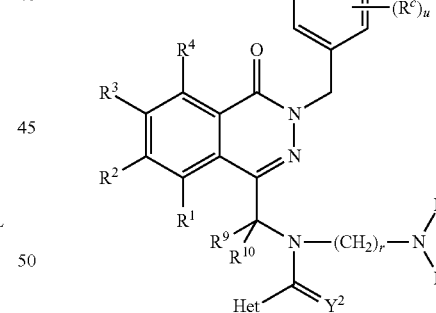

IO

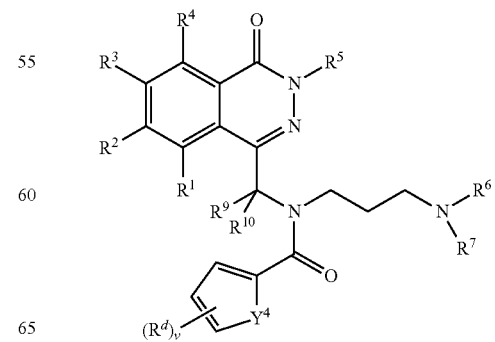

IP in which
R$^1$, R$^2$, R$^3$, R$^4$, R$^5$, R$^6$, R$^7$, R$^8$, R$^9$ and R$^{10}$ have the meanings indicated herein,
r stands for 1, 2, 3 or 4, preferably for 1, 2 or 3 and in particular for 2 or 3,
Y$^2$ stands for O, S or NR$^a$ and in particular for O or S.
Y$^4$ stands for O, S or NR$^a$ and in particular for O or S.
A stands for alkyl,
Ar stands for aryl or heteroaryl, preferably aryl and in particular for unsubstituted or substituted phenyl,
Het stands for heteroaryl,
R$^c$ and R$^d$, independently of one another, are selected from the meanings indicated for R$^1$ to R$^4$, and
u and v, independently of one another, stand for 0, 1, 2 or 3 and in particular for 0, 1 or 2.
R$^c$ is preferably selected from A, CF$_3$, OCF$_3$, OR$^a$, SA, S(O)$_2$A, S(O)A, CH$_2$CN, COOA, CONHA, Hal, SCF, CN and Het, particularly preferably also from H, Cl, Br, F, t-butyl, —CH(CH$_3$)CH$_2$CH$_3$, isopropyl, ethyl and methyl, very particularly preferably selected from t-butyl, isopropyl, ethyl, CF$_3$, methyl, Br, Cl, F, SCF$_3$, CH(CH$_3$)CH$_2$CH$_3$, n-propyl, OCH$_3$, SCH$_3$, n-butyl, CH$_2$CN and Het, and in particular selected from Cl, Br, F, t-butyl, isopropyl, ethyl or CF$_3$.
R$^d$ is preferably selected from A, CF$_3$, OCF$_3$, OR$^a$, SA, S(O)$_2$A, S(O)A, CH$_2$CN, COOA, CONHA, Hal, SCF, CN and Het, particularly preferably also from H, Cl, Br, F, t-butyl, —CH(CH$_3$)CH$_2$CH$_3$, isopropyl, ethyl and methyl, very particularly preferably selected from t-butyl, isopropyl, ethyl, CF$_3$, methyl, Br, Cl, F, SCF$_3$, CH(CH$_3$)CH$_2$CH$_3$, n-propyl, OCH$_3$, SCH$_3$, n-butyl, CH$_2$CN and Het, and in particular selected from Cl, Br, F, t-butyl, isopropyl, ethyl or CF$_3$.

Particular preference is given to compounds according to the invention, i.e. compounds of the formula I and preferably of the formulae I', IA, IB, IC, ID, IE, IF, IG, IH, Ii, IJ, IK and/or IL and preferably of the formulae IM, IN and/or IP, which combine one or preferably more of the preferred embodiments described below in themselves:

A preferred embodiment relates to compounds according to the invention in which
R$^1$ denotes A, CF$_3$, OCF$_3$, SA, SCN, CH$_2$CN, —OCOA, Hal, SCF$_3$, t-butyl, —CH(CH$_3$)CH$_2$CH$_3$, isopropyl, ethyl or methyl.

A further preferred embodiment relates to compounds according to the invention in which
R$^1$ and R$^4$, independently of one another, either denote H or are selected from A, CF$_3$, OCF$_3$, OR$^a$, SA, S(O)$_2$A, S(O)A, CH$_2$CN, COOA, CONHA, Hal, SCF, CN and Het.

A further preferred embodiment relates to compounds according to the invention in which
R$^3$ and R$^4$, independently of one another, are selected from H and Cl.

A further preferred embodiment relates to compounds according to the invention in which
R$^5$ is selected from Ar, aralkyl and heteroaralkyl, preferably from aralkyl and heteroaralkyl and in particular from benzyl and phenethyl;
R$^6$, R$^7$, independently of one another, are selected from H, A, Ar and aralkyl, preferably from H and A and in particular from H, methyl and ethyl; and
R$^8$ is selected from A, Ar and Het, preferably from Ar and Het and in particular from phenyl and pyridyl.

A further preferred embodiment relates to compounds according to the invention in which R$^5$ denotes unsubstituted or substituted benzyl, and
R$^8$ denotes unsubstituted or substituted phenyl.

A further preferred embodiment relates to compounds according to the invention in which R$^6$ and R$^7$, together with the N atom to which they are bonded, form a saturated or unsaturated 5-, 6- or 7-membered heterocycle, which may optionally contain 1, 2 or 3 further heteroatoms selected from N, S and O and which is particularly preferably selected from 1-piperidyl, 4-piperidyl, 1-methylpiperidin-4-yl, 1-piperazyl, 1-(4-methyl)piperazyl, 4-methylpiperazin-1-ylamine, 1-(4-(2-hydroxyethyl))piperazyl, 4-morpholinyl and 1-pyrrolidinyl.

Accordingly, the invention relates, in particular, to the compounds of the formula I in which at least one of the said radicals has one of the preferred meanings indicated above and/or which combine one or more of the preferred embodiments described herein in themselves.

The compounds according to the invention are particularly preferably selected from the compounds (1) to (4):

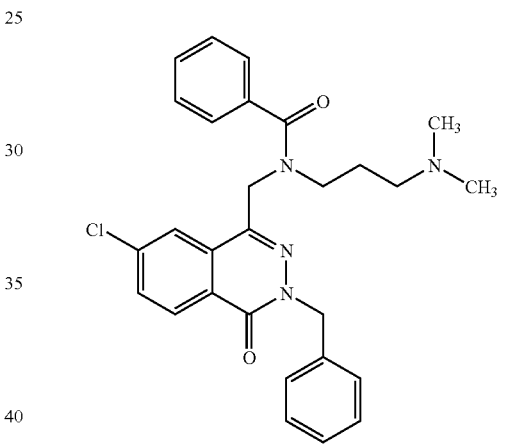

N-(3-benzyl-7-chloro-4-oxo-3,4-dihydrophthalazin-1-ylmethyl)-N-(3-dimethylaminopropyl)benzamide;

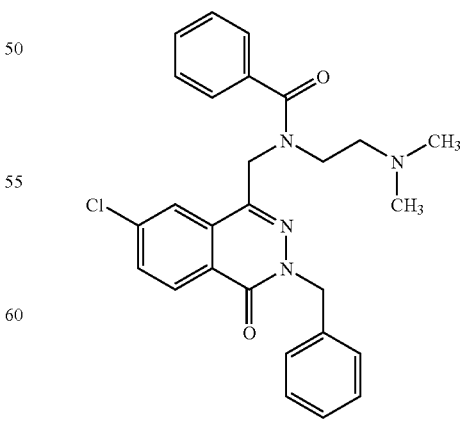

N-(3-benzyl-7-chloro-4-oxo-3,4-dihydrophthalazin-1-ylmethyl)-N-(2-dimethylaminoethyl)benzamide;

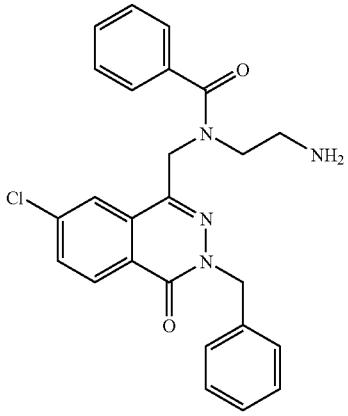

N-(2-aminoethyl)-N-(3-benzyl-7-chloro-4-oxo-3,4-dihydrophthalazin-1-ylmethyl)benzamide;

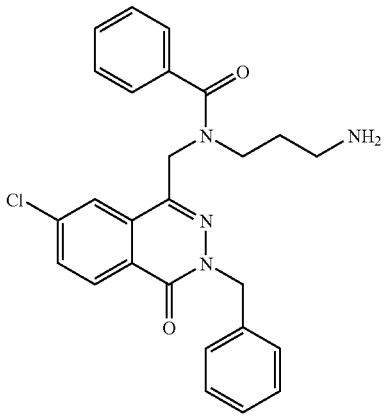

N-(3-aminopropyl)-N-(3-benzyl-7-chloro-4-oxo-3,4-dihydrophthalazin-1-ylmethyl)benzamide;

and the pharmaceutically tolerated derivatives, solvates, salts and stereoisomers thereof, including mixtures of the forms in all ratios, and preferably the salts and/or solvates thereof, and in particular the physiologically tolerated salts and/or solvates thereof.

The compounds according to the invention are furthermore particularly preferably selected from the compounds (5) to (6):

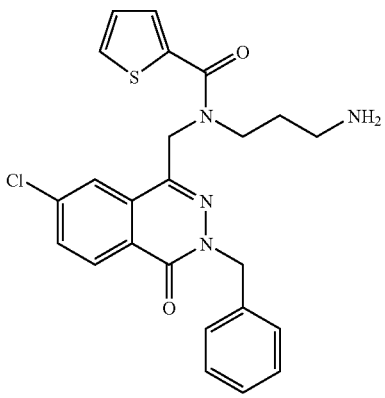

N-(3-aminopropyl)-(3-benzyl-7-chloro-4-oxo-3,4-dihydrophthalazin-1-ylmethyl)thiophene-2-carboxamide;

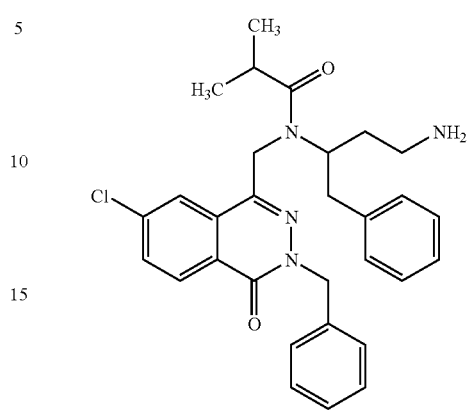

N-(3-amino-1-benzylpropyl)-N-(3-benzyl-7-chloro-4-oxo-3,4-dihydro-phthalazin-1-ylmethyl)isobutyramide;

and the pharmaceutically tolerated derivatives, solvates, salts and stereoisomers thereof, including mixtures of the forms in all ratios, and preferably the salts and/or solvates thereof, and in particular the physiologically tolerated salts and/or solvates thereof.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials may also be formed in situ so that they are not isolated from the reaction mixture, but instead are immediately converted further into the compounds of the formula I.

The reaction is generally carried out in an inert solvent, such as, for example, acetonitrile, preferably in the presence of a base, such as, for example, amines, preferably tertiary amines, hydroxides, in particular alkali metal hydroxides, such as KOH or NaOH, or in particular alkali metal or alkaline-earth metal carbonates, such as $Na_2CO_3$ and $K_2CO_3$. Depending on the conditions used, the reaction time is between a few minutes and 14 days, the reaction temperature is between about 0° and 180°, normally between 0° and 100°, particularly preferably between 15° C. and 60° C., very particularly preferably between 15° C. and 35° C., such as, for example, about 20° C., about 25° C. or about 45 degrees Celsius.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; nitriles, such as acetonitrile; carbon disulfide; carboxylic acids, such as formic acid or acetic acid; nitro compounds, such as nitromethane or nitrobenzene, or mixtures of the said solvents.

If desired, a functionally modified amino and/or hydroxyl group in a compound of the formula I can be liberated by solvolysis or hydrogenolysis by conventional methods. This can be carried out, for example, using NaOH or KOH in water, water/THF or water/dioxane at temperatures between 0 and 100°.

The reduction of an ester to the aldehyde or alcohol or the reduction of a nitrile to the aldehyde or amine is carried out by methods as are known to the person skilled in the art and are described in standard works of organic chemistry.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated, and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition which requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or more usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

The medicaments from Table 1 are preferably, but not exclusively, combined with the compounds of the formula I. A combination of the formula I and medicaments from Table 1 can also be combined with compounds of the formula VI.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 (Hoffmann-La Roche) |
| | Ormiplatin | SM-11355 (Sumitomo) |
| | Iproplatin | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharma) | BNP-1350 (BioNumerik) |
| | Rebeccamycin analogue (Exelixis) | CKD-602 (Chong Kun Dang) |
| | BBR-3576 (Novuspharma) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin | Losoxantrone |
| | | Bleomycin sulfate |

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

The medicaments from Table 1 are preferably, but not exclusively, combined with the compounds of the formula I. A combination of the formula I and medicaments from Table 1 can also be combined with compounds of the formula VI.

TABLE 1-continued

| | | |
|---|---|---|
| | (Daunomycin) | (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxo-rubicin | |
| | Mitoxantrone (Novantrone) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | |
| | | Azaepothilon B (BMS) |
| | BMS 247550 (BMS) | BNP-7787 (BioNumerik) |
| | BMS 184476 (BMS) | CA-4-Prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestane |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | |
| | | Apaziquone (Spectrum Pharmaceuticals) |
| | Albumin + 32P (Isotope Solutions) | |
| | | O6-Benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | | BMS-275291 (Celltech) |
| | Marimastat (British Biotech) | |
| Ribonucleoside reductase inhibitors | | Tezacitabine (Aventis) |
| | | Didox (Molecules for Health) |
| | Gallium maltolate (Titan) | |
| | Triapin (Vion) | |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immuno-modulators | Interferon | Dexosome therapy (Anosys) |
| | Oncophage (Antigenics) | |
| | GMK (Progenics) | Pentrix (Australian Cancer Technology) |
| | Adenocarcinoma vaccine | |

TABLE 1-continued

| | | |
|---|---|---|
| | (Biomira)<br>CTP-37 (AVI BioPharma)<br>JRX-2 (Immuno-Rx)<br>PEP-005 (Peplin Biotech)<br>Synchrovax vaccines (CTL Immuno)<br>Melanoma vaccine (CTL Immuno)<br>p21-RAS vaccine (GemVax) | JSF-154 (Tragen)<br>Cancer vaccine (Intercell)<br>Norelin (Biostar)<br>BLP-25 (Biomira)<br>MGV (Progenics)<br>!3-Alethin (Dovetail)<br>CLL-Thera (Vasogen) |
| Hormonal and antihormonal agents | Oestrogens<br>Conjugated oestrogens<br>Ethynyloestradiol<br>chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (EntreMed)<br>Arzoxifen (Eli Lilly) |
| Photodynamic agents | Talaporfin (Light Sciences)<br>Theralux (Theratechnologies)<br>Motexafin-Gadolinium (Pharmacyclics) | Pd-Bacteriopheophorbid (Yeda)<br>Lutetium-Texaphyrin (Pharmacyclics)<br>Hypericin |
| Tyrosine kinase inhibitors | Imatinib (Novartis)<br>Leflunomide (Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmithKline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-IOO (gal3 antagonist, GlycoGenesys)<br>G17DT immunogen (gastrin inhibitor, Aphton)<br>Efaproxiral (oxygenator, Allos Therapeutics)<br>PI-88 (heparanase inhibitor, Progen)<br>Tesmilifen (histamine antagonist, YM BioSciences)<br>Histamine (histamine H2 receptor agonist, Maxim)<br>Tiazofurin (IMPDH inhibitor, Ribapharm)<br>Cilengitide (integrin | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore)<br>3CPA (NF-kappaB inhibitor, Active Biotech)<br>Seocalcitol (vitamin D receptor agonist, Leo)<br>131-I-TM-601 (DNA antagonist, TransMolecular)<br>Eflornithin (ODC inhibitor, ILEX Oncology)<br>Minodronic acid (osteoclast inhibitor, Yamanouchi)<br>Indisulam (p53 stimulant, Eisai)<br>Aplidin (PPT inhibitor, PharmaMar) |

TABLE 1-continued

| | |
|---|---|
| antagonist, Merck KGaA) | Rituximab (CD20 antibody, |
| SR-31747 (IL-1 antagonist, | Genentech) |
| Sanofi-Synthelabo) | Gemtuzumab (CD33 |
| CCI-779 (mTOR kinase | antibody, Wyeth Ayerst) |
| inhibitor, Wyeth) | PG2 (haematopoiesis |
| Exisulind (PDE-V inhibitor, | promoter, Pharmagenesis) |
| Cell Pathways) | Immunol ™ (triclosan |
| CP-461 (PDE-V inhibitor, | mouthwash, Endo) |
| Cell Pathways) | Triacetyluridine (uridine |
| AG-2037 (GART inhibitor, | prodrug, Wellstat) |
| Pfizer) | SN-4071 (sarcoma agent, |
| WX-UK1 (plasminogen | Signature BioScience) |
| activator inhibitor, Wilex) | TransMID-107 ™ |
| PBI-1402 (PMN stimulant, | (immunotoxin, KS |
| ProMetic LifeSciences) | Biomedix) |
| Bortezomib (proteasome | PCK-3145 (apoptosis |
| inhibitor, Millennium) | promoter, Procyon) |
| SRL-172 (T-cell stimulant, | Doranidazole (apoptosis |
| SR Pharma) | promoter, Pola) |
| TLK-286 (glutathione-S | CHS-828 (cytotoxic agent, |
| transferase inhibitor, Telik) | Leo) |
| PT-100 (growth factor | Trans-retinoic acid |
| agonist, Point | (differentiator, NIH) |
| Therapeutics) | MX6 (apoptosis promoter, |
| Midostaurin (PKC inhibitor, | MAXIA) |
| Novartis) | Apomine (apoptosis |
| Bryostatin-1 (PKC | promoter, ILEX Oncology) |
| stimulant, GPC Biotech) | Urocidin (apoptosis |
| CDA-II (apoptosis | promoter, Bioniche) |
| promoter, Everlife) | Ro-31-7453 (apoptosis |
| SDX-101 (apoptosis | promoter, La Roche) |
| promoter, Salmedix) | Brostallicin (apoptosis |
| Ceflatonin (apoptosis | promoter, Pharmacia) |
| promoter, ChemGenex) | |

The compounds of the formula I are preferably combined with known anticancer agents:

These known anti-cancer agents include the following: oestrogen receptor modulators, androgen receptor modulators, retinoid receptor modulators, cytotoxic agents, antiproliferative agents, prenyl protein transferase inhibitors, HMG-CoA reductase inhibitors, HIV protease inhibitors, reverse transcriptase inhibitors and other angiogenesis inhibitors. The present compounds are particularly suitable for administration at the same time as radiotherapy. The synergistic effects of inhibition of VEGF in combination with radiotherapy have been described by specialists (see WO 00/61186).

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]-phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)mu-[diamineplatinum(II)]bis-[diamine(chloro)platinum(II)]tetrachloride, diarisidinylspermine, arsenic tri-oxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplastone, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS 188797. Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4': b,7]indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, neizarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]-glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 1 1-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Particular preference is given to the use of the compound according to the invention for the treatment and prophylaxis of tumour diseases.

The tumour is preferably selected from the group of tumours of the squamous epithelium, the bladder, the stomach, the kidneys, the head and neck, the oesophagus, the cervix, the thyroid, the intestine, the liver, the brain, the prostate, the urogenital tract, the lymphatic system, the larynx and/or the lung.

The tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myelocytic leukaemia, chronic myelocytic leukaemia, acute lymphatic leukaemia and/or chronic lymphatic leukaemia.

The invention also encompasses a method for the treatment of a patient who has a neoplasm, such as a cancer, by administration of
a) one or more of the compounds of the formula I:
b) and one or more of the compounds of the formula VI or acid-addition salts thereof, in particular hydrochlorides:

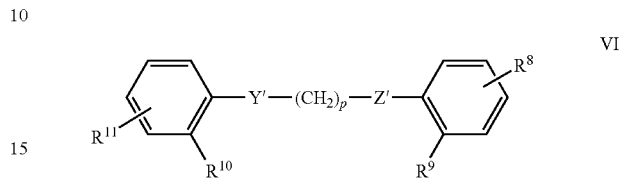

in which Y' and Z' each, independently of one another, denote O or N, $R^6$ and $R^7$ each, independently of one another, denote H, OH, halogen, OC1-10-alkyl, $OCF_3$, $NO_2$ or $NH_2$, n denotes an integer between 2 and 6, each inclusive, and $R^8$ and $R^9$ are each, independently of one another, preferably in the meta- or para-position and are selected from the group:

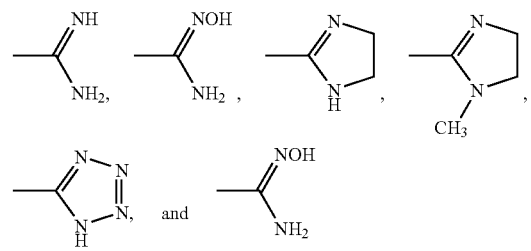

where the first and second compound are administered simultaneously or within 14 days of one another in amounts which are sufficient to inhibit the growth of the neoplasm.

The combination of the compounds of the formula I with the compounds of the formula VI and other pentamidine analogues results in a synergistic action in the inhibition of neoplasias. Combinations comprising the compounds of the formula VI are mentioned, for example, in WO 02058684.

The mechanism of action of pentamidine or derivatives thereof has not been clearly explained at present: pentamidine or derivatives thereof appears to have pleiotropic actions since it results in a decrease in DNA, RNA and protein synthesis. It was recently described that pentamidine is a capable inhibitor of PRL1, -2 and -3 phosphatases (Pathak et al., 2002) and tyrosine phosphatases, and overexpression thereof is accompanied by neoplastic malignant tumours in humans. On the other hand, it has been described that pentamidine is a medicament which binds to the DNA minor groove (Puckowska et al., 2004) and is able to exert its action via disturbance of gene expression and/or DNA synthesis.

Experiments show that:
both pentamidine and also preferably the compounds of the formula I maintain cells in the G2/M cell cycle.
the combination of pentamidine and compounds of the formula I has preferably additive to synergistic actions on cell proliferation.

Other suitable pentamidine analogues include stilbamidine (G-1) and hydroxystilbamidine (G-2) and indole analogues thereof (for example G-3):

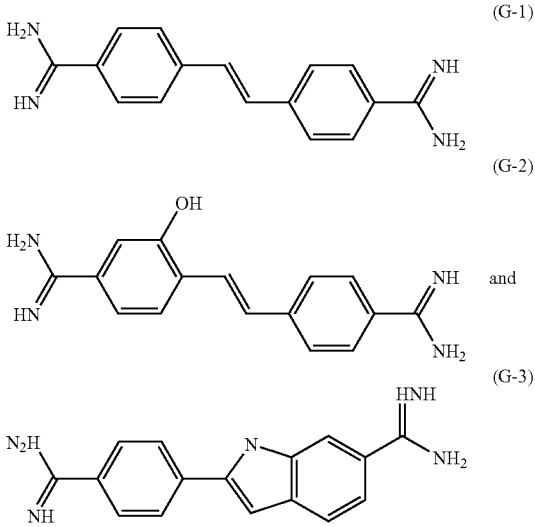

Each amidine unit may be replaced, independently of one another, by one of the units defined above for $R^8$ and $R^{11}$. As in the case of benzimidazoles and pentamidines, salts of stilbamidine, hydroxystilbamidine and indole derivatives thereof are also suitable for the process according to the invention. Preferred salts include, for example, dihydrochloride and methanesulfonate salts.

Still other analogues are those which fall under a formula which is provided in one of the U.S. Pat. Nos. 5,428,051, 5,521,189, 5,602,172, 5,643,935, 5,723,495, 5,843,980, 6,172,104 and 6,326,395 or the US patent application with the publication No. US 2002/0019437 A1, each of which is incorporated in its entirety by way of reference. Illustrative analogues include 1,5-bis(4'-(N-hydroxyamidino)phenoxy) pentane, 1,3-bis(4'-(N-hydroxyamidino)phenoxy)propane, 1,3-bis(2'-methoxy-4'-(N-hydroxyamidino)phenoxy)propane, 1,4-bis-(4'-(N-hydroxyamidino)phenoxy)butane, 1,5-bis(4'-(N-hydroxyamidino)phenoxy)pentane, 1,4-bis(4'-(N-hydroxyamidino)phenoxy)butane, 1,3-bis(4'-(4-hydroxyamidino)phenoxy)propane, 1,3-bis(2'-methoxy-4'-(N-hydroxyamidino)phenoxy)propane, 2,5-bis[4-amidinophenyl]furan, 2,5-bis[4-amidinophenyl]furan bisamide oxime, 2,5-bis[4-amidinophenyl]furan bis-O-methylamide oxime, 2,5-bis[4-amidinophenyl]furan bis-O-ethylamide oxime, 2,8-diamidinodibenzothiophene, 2,8-bis(N-isopropylamidino)carbazole, 2,8-bis(N-hydroxyamidino)carbazole, 2,8-bis(2-imidazolinyl) dibenzothiophene, 2,8-bis-(2-imidazolinyl)-5,5-dioxodibenzothiophene, 3,7-diamidinodibenzothiophene, 3,7-bis(N-isopropylamidino)dibenzothiophene, 3,7-bis(N-hydroxyamidino)dibenzothiophene, 3,7-diaminodibenzothiophene, 3,7-dibromodibenzothiophene, 3,7-dicyanodibenzothiophene, 2,8-diamidinodibenzofuran, 2,8-di-(2-imidazolinyl)dibenzofuran, 2,8-di-(N-isopropylamidino) dibenzofuran, 2,8-di-(N-hydroxyamidino)dibenzofuran, 3,7-di-(2-imidazolinyl)dibenzofuran, 3,7-di-(isopropylamidino) dibenzofuran, 3,7-di-(A-hydroxyamidino)dibenzofuran, 2,8-dicyanodibenzofuran, 4,4'-dibromo-2,2'-dinitrobiphenyl, 2-methoxy-2'-nitro-4,4'-dibromobiphenyl, 2-methoxy-2'-amino-4,4'-dibromobiphenyl, 3,7-di-bromodibenzofuran, 3,7-dicyanodibenzofuran, 2,5-bis(5-amidino-2-benzimidazolyl)pyrrole, 2,5-bis[5-(2-imidazolinyl)-2-benzimidazolyl] pyrrole, 2,6-bis[5-(2-imidazolinyl)-2-benzimidazolyl]pyridine, 1-methyl-2,5-bis(5-amidino-2-benzimidazolyl) pyrrole, 1-methyl-2,5-bis[5-(2-imidazolyl)-2-benzimidazolyl]pyrrole, 1-methyl-2,5-bis[5-(1,4,5,6-tetrahydro-2-pyrimidinyl)-2-benzimidazolyl]pyrrole, 2,6-bis (5-amidino-2-benzimidazolyl)pyridine, 2,6-bis[5-(1,4,5,6-tetrahydro-2-pyrimidinyl)-2-benzimidazolyl]pyridine, 2,5-bis(5-amidino-2-benzimidazolyl)furan, 2,5-bis[5-(2-imidazolinyl)-2-benzimidazolyl]-furan, 2,5-bis(5-N-isopropylamidino-2-benzimidazolyl)furan, 2,5-bis(4-guanylphenyl)furan, 2,5-bis(4-guanylphenyl)-3,4-dimethylfuran, 2,5-di-p-[2-(3,4,5,6-tetrahydropyrimidyl) phenyl]furan, 2,5-bis[4-(2-imidazolinyl)phenyl]furan, 2,5-[bis{4-(2-tetrahydropyrimidinyl)}phenyl]-p-(tolyloxy) furan, 2,5-[bis{4-(2-imidazolinyl)}phenyl]-3-p-(tolyloxy) furan, 2,5-bis{4-[5-(N-2-aminoethylamido)benzimidazol-2-yl]phenyl}furan, 2,5-bis[4-(3a,4,5,6,7,7a-hexahydro-1H-benzimidazol-2-yl)phenyl]furan, 2,5-bis[4-(4,5,6,7-tetrahydro-1H-1,3-diazepin-2-yl)phenyl]furan, 2,5-bis(4-N,N-dimethylcarboxhydrazidophenyl)furan, 2,5-bis{4-[2-(N-2-hydroxyethyl)imidazolinyl]phenyl}furan, 2,5-bis[4-(N-isopropylamidino)phenyl]furan, 2,5-bis{4-[3-(dimethylaminopropyl)amidino]phenyl}furan, 2,5-bis{4-[N-(3-aminopropyl)amidino]phenyl}furan, 2,5-bis[2-(imidzazolinyl)phenyl]-3,4-bis(methoxymethyl)furan, 2,5-bis[4-N-(dimethylaminoethyl)guanyl]phenylfuran, 2,5-bis{4-[(N-2-hydroxyethyl)guanyl]phenyl}furan, 2,5-bis[4-N-(cyclopropylguanyl)phenyl]furan, 2,5-bis[4-(N,N-diethylaminopropyl)guanyl]phenylfuran, 2,5-bis{4-[2-(N-ethylimidazolinyl)]phenyl}furan, 2,5-bis{4-[N-(3-pentylguanyl)]}phenylfuran, 2,5-bis[4-(2-imidazolinyl) phenyl]-3-methoxyfuran, 2,5-bis[4-(N-isopropylamidino) phenyl]-3-methylfuran, bis[5-amidino-2-benzimidazolyl] methane, bis[5-(2-imidazolyl)-2-benzimidazolyl]-methane, 1,2-bis[5-amidino-2-benzimidazolyl]ethane, 1,2-bis[5-(2-imidazolyl)-2-benzimidazolyl]ethane, 1,3-bis[5-amidino-2-benzimidazolyl]propane, 1,3-bis[5-(2-imidazolyl)-2-benzimidazolyl]propane, 1,4-bis[5-amidino-2-benzimidazoiyl] propane, 1,4-bis[5-(2-imidazolyl)-2-benzimidazolyl]butane, 1,8-bis[5-amidino-2-benzimidazolyl]octane, trans-1,2-bis [5-amidino-2-benzimidazolyl]ethene, 1,4-bis[5-(2-imidazolyl)-2-benzimidazolyl]-1-butene, 1,4-bis[5-(2-imidazolyl)-2-benzimidazolyl]-2-butene, 1,4-bis[5-(2-imidazolyl)-2-benzimidazolyl]-1-methylbutane, 1,4-bis[5-(2-imidazolyl)-2-benzimidazolyl]-2-ethylbutane, 1,4-bis[5-(2-imidazolyl)-2-benzimidazolyl]-1-methyl-1-butene, 1,4-bis[5-(2-imidazolyl)-2-benzimidazolyl]-2,3-diethyl-2-butene, 1,4-bis[5-(2-imidazolyl)-2-benzimidazolyl]-1,3-butadiene, 1,4-bis[5-(2-imidazolyl)-2-benzimidazolyl]-2-methyl-1, 3-butadiene, bis[5-(2-pyrimidyl)-2-benzimidazolyl]-methane, 1,2-bis[5-(2-pyrimidyl)-2-benzimidazolyl]ethane, 1,3-bis[5-amidino-2-benzimidazolyl]propane, 1,3-bis[5-(2-pyrimidyl)-2-benzimidazolyl]propane, 1,4-bis[5-(2-pyrimidyl)-2-benzimidazolyl]butane, 1,4-bis[5-(2-pyrimidyl)-2-benzimidazolyl]-1-butene, 1,4-bis[5-(2-pyrimidyl)-2-benzimidazolyl]-2-butene, 1,4-bis[5-(2-pyrimidyl)-2-benzimidazolyl]-1-methylbutane, 1,4-bis[5-(2-pyrimidyl)-2-benzimidazolyl]-2-ethylbutane, 1,4-bis[5-(2-pyrimidyl)-2-benzimidazolyl]-1-methyl-1-butene, 1,4-bis[5-(2-pyrimidyl)-2-benzimidazolyl]-2,3-diethyl-2-butene, 1,4-bis[5-(2-pyrimidyl)-2-benzimidazolyl]-1,3-butadiene and 1,4-bis[5-(2-pyrimidyl)-2-benzimidazolyl]-2-methyl-1,3-butadiene, 2,4-bis(4-guanylphenyl)pyrimidine, 2,4-bis(4-imidazolin-2-yl)pyrimidine, 2,4-bis[(tetrahydropyrimidinyl-2-yl)phenyl]pyrimidine, 2-(4-[N-i-propylguanyl]phenyl)-4-(2-methoxy-4-[N-i-propylguanyl]phenyl)pyrimidine, 4-(N-cyclopentylamidino)-1,2-phenylenediamine, 2,5-bis[2-(5- amidino)benzimidazoyl]furan, 2,5-bis[2-{5-(2-imidazolino)}benzimidazoyl]furan, 2,5-bis[2-(5-N-isopropylamidino)benzimidazoyl]furan, 2,5-bis[2-(5-N-cyclopentylamid ino)benzimidazoyl]furan, 2,5-bis[2-(5-amidino)benzimidazoyl]pyrrole, 2,5-bis[2-{5-(2-imidazolino)}benzimidazoyl]pyrrole, 2,5-bis[2-(5-N-isopropylamidino)benzimidazoyl]pyrrole, 2,5-bis[2-(5-N-cyclopentylamidino)benzimidazoyl]pyrrole, 1-methyl-2,5-bis[2-(5-amidino)benzimidazoyl]pyrrole, 2,5-bis[2-{5-(2-imidazolino)}benzimidazoyl]-1-methylpyrrole, 2,5-bis[2-(5-N-cyclopentylamidino)benzimidazoyl]-1-methylpyrrole, 2,5-bis[2-(5-N-isopropylamidino)benzimidazoyl]thiophene, 2,6-bis[2-{5-(2-imidazolino)}benzimidazoyl]pyridine, 2,6-bis[2-(5-amidino)benzimidazoyl]pyridine, 4,4'-bis[2-(5-N-isopropylamidino)benzimidazoyl]-1,2-diphenylethane, 4,4'-bis[2-(5-N-cyclopentylamidino)benzimidazoyl]-2,5-diphenylfuran, 2,5-bis[2-(5-amidino)benzimidazoyl]benzo[b]furan, 2,5-bis-[2-(5-N-cyclopentylamidino)benzimidazoyl]benzo[b]furan, 2,7-bis[2-(5-N-iso-propylamidino)benzimidazoyl]fluorine, 2,5-bis[4-(3-(N-morpholinopropyl)-carbamoyl)phenyl]furan, 2,5-bis[4-(2-N,N-dimethylaminoethylcarbamoyl)phenyl]furan, 2,5-bis[4-(3-N,N-dimethylaminopropylcarbamoyl)phenyl]furan, 2,5-bis[4-(3-N-methyl-3-N-phenylaminopropylcarbamoyl)phenyl]furan, 2,5-bis[4-(3-N,N8,N11-trimethylaminopropylcarbamoyl)phenyl]furan, 2,5-bis[3-amidinophenyl]furan, 2,5-bis[3-(N-isopropylamidino)amidinophenyl]furan, 2,5-bis[3-[(N-(2-dimethylaminoethyl)amidino]phenylfuran, 2,5-bis[4-(N-2,2,2-trichloroethoxycarbonyl)amidinophenyl]furan, 2,5-bis[4-(N-thioethylcarbonyl)-amidinophenyl]furan, 2,5-bis[4-(N-benzyloxycarbonyl)amidinophenyl]furan, 2,5-bis[4-(N-phenoxycarbonyl)amidinophenyl]furan, 2,5-bis[4-(N-(4-fluoro)phenoxycarbonyl)amidinophenyl]furan, 2,5-bis[4-(N-(4-methoxy)phenoxycarbonyl)amidinophenyl]furan, 2,5-bis[4-(1-acetoxyethoxycarbonyl)amidinophenyl]furan and 2,5-bis[4-(N-(3-fluoro)phenoxycarbonyl)amidinophenyl]-furan. Processes for the preparation of one of the above compounds are described in U.S. Pat. Nos. 5,428,051, 5,521,189, 5,602,172, 5,643,935, 5,723,495, 5,843,980, 6,172,104 and 6,326,395 or the US patent application with the publication No. US 2002/0019437 A1.

Pentamidine metabolites are likewise suitable in the antiproliferative combination according to the invention. Pentamidine is rapidly metabolised in the body to at least seven primary metabolites. Some of these metabolites have one or more actions in common with pentamidine. Pentamidine metabolites have an antiproliferative action when combined with a benzimidazole or an analogue thereof.

Seven pentamidine analogues are shown below.

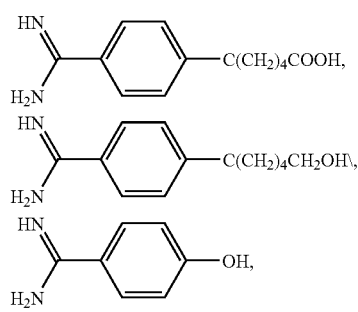

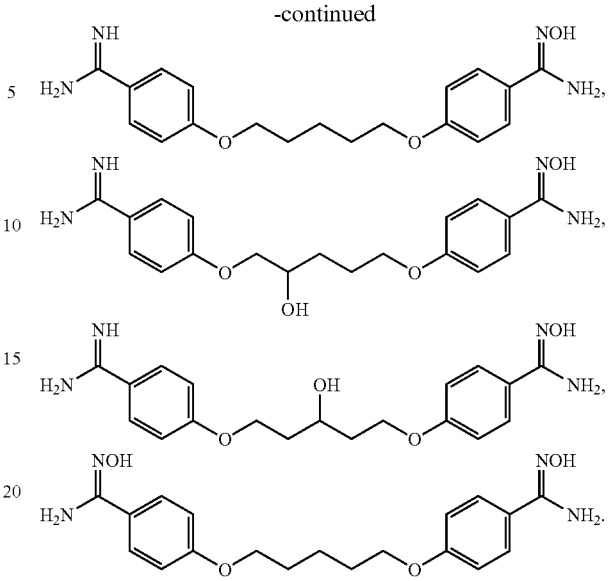

The combinations according to the invention of compounds of the formula I and formula VI or analogues thereof and metabolites thereof are suitable for the treatment of neoplasms. Combination therapy can be carried out alone or in combination with another therapy (for example operation, irradiation, chemotherapy, biological therapy). In addition, a person whose risk of developing a neoplasm is greater (for example someone who is genetically predisposed or someone who previously had a neoplasm) can be given prophylactic treatment in order to inhibit or delay neoplasm formation.

The invention likewise relates to the combination of kinesin ATPase Eg5/KSP with the compounds of the formula VI, pentamidine, analogues thereof and/or metabolites thereof.

The dosage and frequency of administration of each compound in the combination can be controlled independently. For example, one compound may be administered orally three times daily, while the second compound may be administered intramuscularly once per day. The compounds may also be formulated together, leading to administration of both compounds.

The antiproliferative combinations according to the invention can also be provided as components of a pharmaceutical package. The two medicaments can be formulated together or separately and in individual dosage amounts.

Under another aspect, the invention encompasses the treatment of a patient who has a neoplasm, such as a cancer, by administration of a compound of the formulae (I) and (VI) in combination with an antiproliferative agent. Suitable antiproliferative agents include those provided in Table 1.

The following examples are intended to help the person skilled in the art to understand the present invention better with reference to the experiments specifically explained below and the results of these experiments. However, the examples are not intended to restrict the present invention and the scope of protection defined by the patent claims. The characteristics, features, properties, advantages and/or uses mentioned in the examples of the compounds mentioned in the examples can also be applied to other compounds, uses and other subject-matters according to the invention which are encompassed by the patent claims, but are not mentioned in the examples.

Above and below, all temperatures are indicated in ° C. In the following examples, "conventional work-up" means: if necessary, water is added, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) M+

FAB (fast atom bombardment) (M+H)+

ESI (electrospray ionisation) (M+H)+

APCI-MS (atmospheric pressure chemical ionisation-mass spectrometry) (M+H)+

EXAMPLES

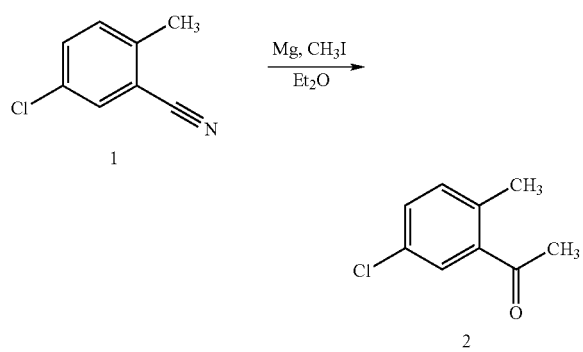

9.62 g (0.4 mol) of magnesium are initially introduced into a flask, a small grain of iodine is added, and 24.7 ml (0.4 mol) of methyl iodide in 200 ml of anhydrous diethyl ether are subsequently slowly added dropwise. The mixture begins to boil rapidly during this addition. When the addition is complete, the mixture is stirred for a further half an hour. A solution of 20 g (0.13 mol) of 5-chloro-2-methylbenzonitrile 1 in 120 ml of anhydrous diethyl ether is slowly added dropwise to the prepared solution at room temperature, and, when the addition is complete, the mixture is stirred under reflux overnight. The suspension is poured into 2 l of ice-water, 800 ml of 20% sulfuric acid are added, and the mixture is subsequently stirred at 40° C. for 1 h. The ether phase is separated off, the aqueous phase is extracted 5 times with ether, and the combined organic phases are washed with water until neutral, dried using Na$_2$SO$_4$, filtered and evaporated.

Yield: 21.2 g (95%) of 2, yellow-brown oil

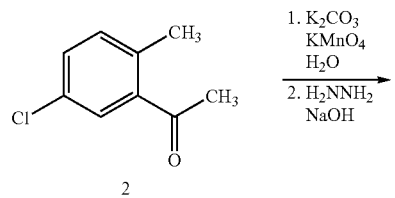

-continued

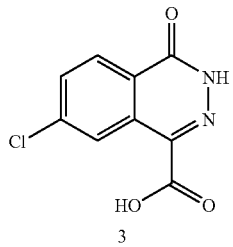

1) 21.2 g (0.12 mol) of 2 are initially introduced in 300 ml of water together with 10.09 g (0.073 mol) of potassium carbonate, and the mixture is heated to reflux with stirring. A solution of 77.8 g (0.49 mol) of potassium permanganate in 1.1 l of water is then added dropwise. When the addition is complete, the boiling is continued overnight. The brown suspension is cooled to about 50° C., filtered through kieselguhr with suction and rinsed with water. The pale-yellow, clear filtrate is concentrated to half (about 600 ml) in a rotary evaporator and reacted further without purification.

2) The solution is warmed to about 90° C., neutralised (pH 8) using 2N HCl, and a hot solution of 16 g (0.12 mol) of hydrazinium sulfate and 5.4 g (0.135 mol) of sodium hydroxide in 50 ml of water is subsequently added. When the addition is complete, the solution is stirred under reflux for a further 2 h. The solution is concentrated to about half in a rotary evaporator, during which a solid precipitates. This is filtered off with suction and rinsed with a little water. Further crystalline product is precipitated from the alkaline filtrate using conc. HCl, washed with water and dried in vacuo. The two crystal batches are combined.

Yield: 7.6 g (27%) of 3, colourless solid

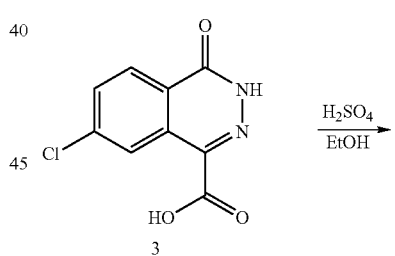

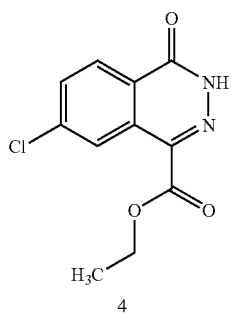

7.6 g (33 mmol) of 3 are suspended in 350 ml of ethanol, and 17.6 ml (0.33 mol) of conc. sulfuric acid are added in portions with stirring. When the addition is complete, the reaction mixture is boiled under reflux overnight. The suspension is cooled to room temperature and poured into about 600 ml of ice-water. The precipitated solid is filtered off with suction, rinsed with water and dried at 40° C. in vacuo.

Yield: 8.06 g (90%) of 4, colourless crystals

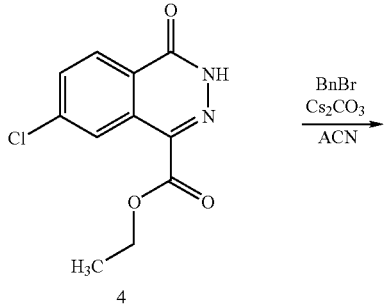

7.58 g (29.99 mmol) of 4 and 10.26 g (31.49 mmol) of caesium carbonate are initially introduced in 150 ml of acetonitrile (ACN), and 3.74 ml (31.49 mmol) of benzyl bromide are added. The reaction mixture is boiled under reflux for 2 h, filtered while hot and rinsed with about 20 ml of each of ACN and ethyl acetate. The filtrate is evaporated, and the residue is partitioned between ethyl acetate and water. The organic phase is separated off, and the aqueous phase is extracted a further 1× with ethyl acetate. The combined organic phases are washed 2× with water and 1× with saturated NaCl solution, dried using $Na_2SO_4$, filtered and evaporated. The residue is digested using petroleum ether, filtered off with suction, rinsed with petroleum ether and subsequently dried at 35° C. in vacuo.

Yield: 9.21 g (84%) of 5, colourless solid

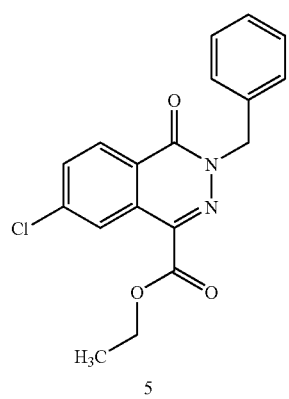

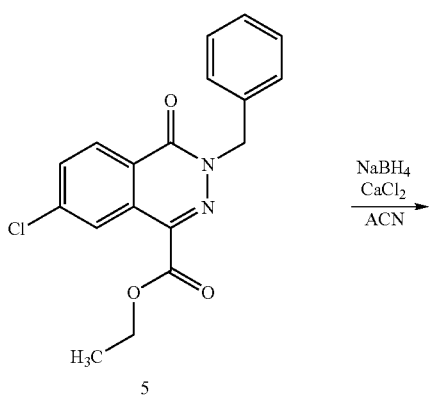

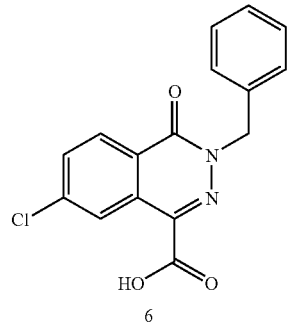

2.5 g (7.29 mmol) of 5 and 414 mg (10.94 mmol) of sodium borohydride are suspended in 40 ml of ethanol, and a solution of 405 mg (3.65 mmol) of calcium chloride in 10 ml of ethanol is added at room temperature. The reaction mixture is stirred at 20-25° C. for 2 h, diluted with 150 ml of water and adjusted to pH 2-3 using 1 N HCl. The aqueous solution is extracted 3× with ethyl acetate. The combined organic phases are washed 1× with sat. $NaHCO_3$ solution, 1× with water and 1× with sat. NaCl solution, dried using $Na_2SO_4$, filtered and evaporated.

Yield: 2.2 g (100%) of 6, colourless solid

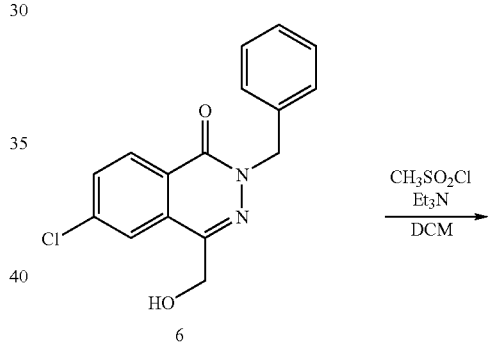

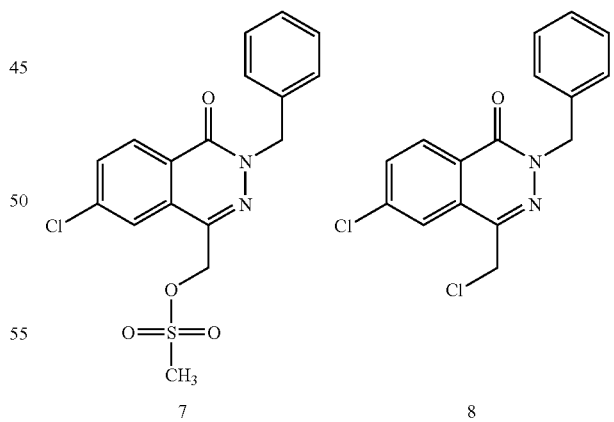

273 mg (0.91 mmol) of 6 are dissolved in 7 ml of dichloromethane (DCM), and 252 µl (1.82 mmol) of triethylamine are added. A solution of 78 µl (1 mmol) of methanesulfonyl chloride in 2.5 ml of DCM is subsequently added dropwise. The reaction mixture is stirred at room temperature for 10 min, diluted with DCM, washed 3× with water and 1× with saturated NaCl solution, dried using $Na_2SO_4$, filtered and evaporated. The residue is purified by chromatography (40 g of silica gel, eluent: petroleum ether/ethyl acetate 8:2–7:3 in 60 min).

Yield: 233 mg (66%) of 7, colourless solid
43 mg (15%) of 8, colourless solid

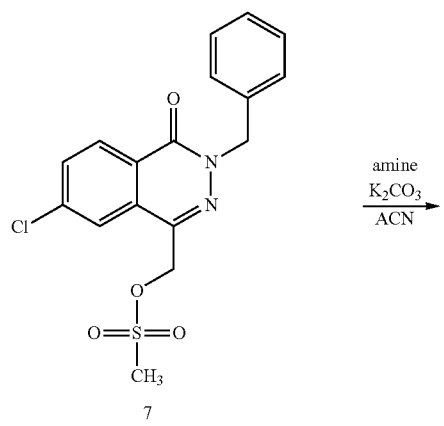

7

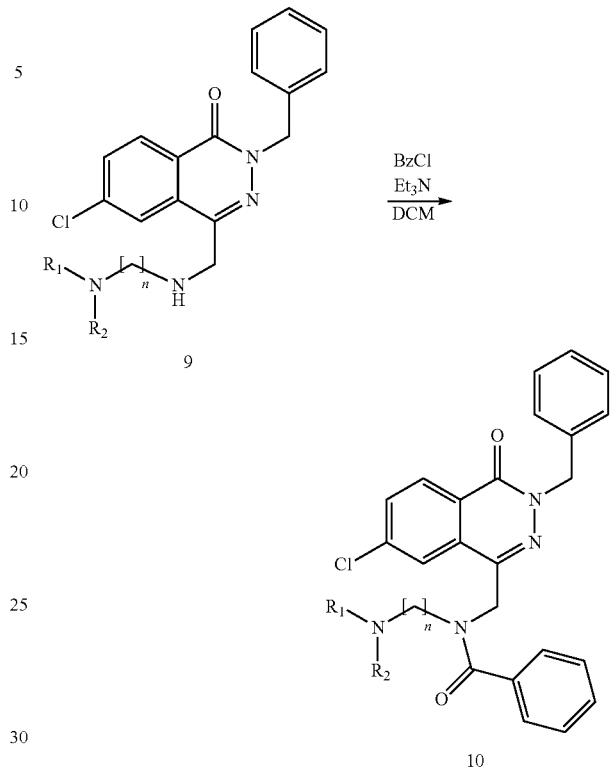

9

10

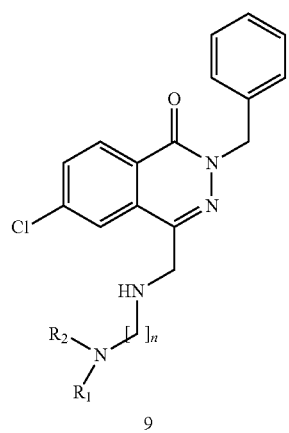

9

0.1 mmol of 7 is initially introduced together with potassium carbonate (1 equivalent), a solution of the corresponding amine (3 equivalents) in ACN is added, and the mixture is stirred at room temperature or 45° C. until the reaction is complete. The reaction mixture is diluted with water, adjusted to pH 9-10 using 1 N NaOH and extracted with ethyl acetate. The aqueous phase is extracted a further 2× with ethyl acetate. The combined organic phases are washed 1× with saturated NaCl solution, dried using $Na_2SO_4$, filtered and evaporated. The residue is purified by chromatography (4 g of silica gel, eluent: DCM/MeOH 7.5%+0.1% of $NH_3$).

9a: Reaction with N,N-dimethylethylenediamine ($R_1$, $R_2$=$CH_3$, n=2) 1 h at 45° C.; yield: 53%, colourless oil 9b: Reaction with N,N-dimethylpropylenediamine ($R_1$, $R_2$=$CH_3$, n=3) 1.5 h at room temperature; yield: 37%, colourless oil 9c: Reaction with N-BOC-ethylenediamine ($R_1$=BOC, $R_2$=H, n=2) 1 h at 45° C.; yield: 85%, colourless oil 9d: Reaction with N-BOC-propylenediamine ($R_1$=BOC, $R_2$=H, n=3) 1 h at 45° C.; yield: 72%, colourless oil 0.06 mmol of 9a-d is dissolved in 750 µl of DCM with stirring, triethylamine (1.1 equivalents) is added, and benzoyl chloride (1.1 equivalents) is added dropwise. The reaction mixture is stirred at room temperature until the reaction is complete, diluted with DCM, washed 3× with water and 1× with saturated NaCl solution, dried using $Na_2SO_4$, filtered and evaporated.

10a: from 9a ($R_1$, $R_2$=$CH_3$, n=2); 1 h; yield: 91%, colourless oil

10b: from 9b ($R_1$, $R_2$=$CH_3$, n=3); 30 min; purification by chromatography (RP-18 column); yield: 61%, colourless oil 10c: from 9c ($R_1$=BOC, $R_2$=H, n=2); 30 min; yield: 85%, colourless oil 10d: from 9d ($R_1$=BOC, $R_2$=H, n=3); 1 h; yield: 88%, colourless oil

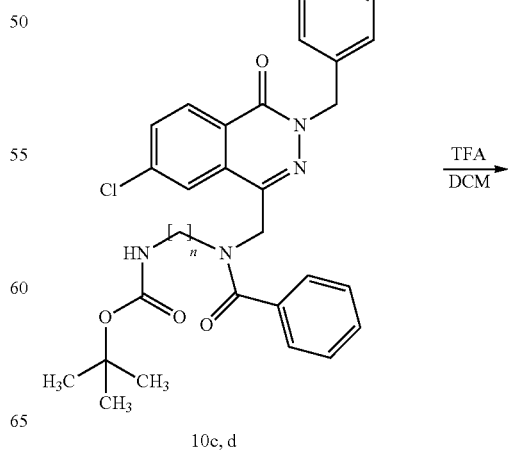

10c, d

-continued

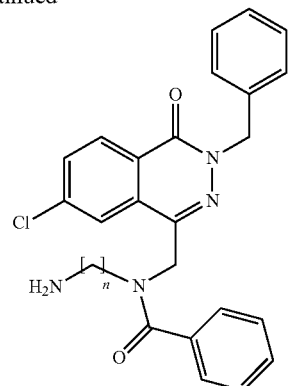

11a, b

Compounds 10c,d are dissolved in DCM, trifluoroacetic acid (30 equivalents) is added, and the mixture is stirred at room temperature for 1 h. The reaction mixture is evaporated, the residue is taken up in ethyl acetate, and the solution is extracted with saturated NaHCO₃ solution. The organic phase is washed 1× with water and 1× with saturated NaCl solution, dried using Na₂SO₄, filtered and evaporated. The residue is purified by chromatography (4 g of silica gel, eluent: DCM/MeOH 5.5%+0.1% of NH₃).

11a: from 10c (n=2); yield: 75%, colourless solid
11b: from 10d (n=3); yield: 82%, colourless oil Further compounds according to the invention are obtained analogously using the corresponding precursors.

For example, the following compounds (12, 13) are advantageously obtained in accordance with the following reaction schemes:

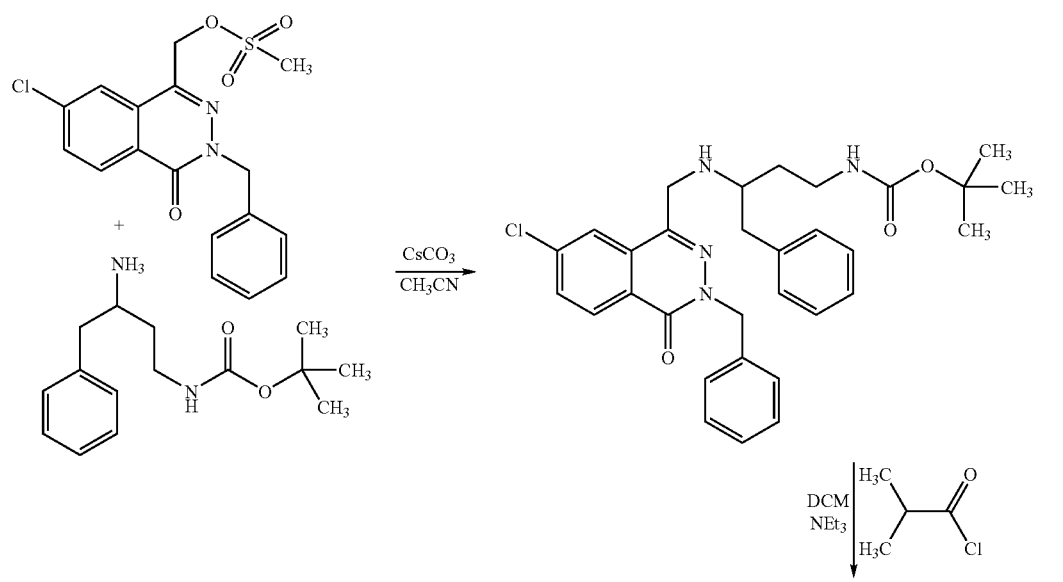

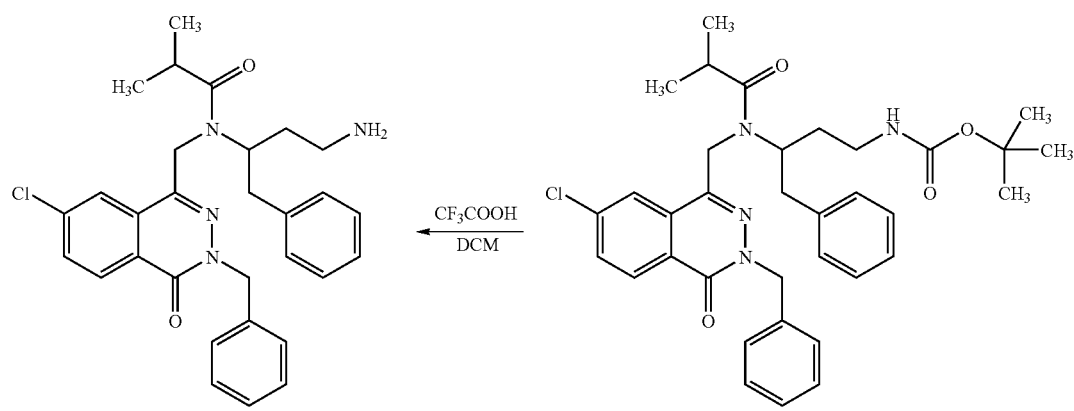

12

Compound 12 obtained in accordance with the above reaction scheme can be characterised by HPLC chromatography (column: Chromolith SpeedROD RP18e 50-4.6; gradient 5.5 min./flow rate: 2.75 ml (90:10-0:100 (H₂O+0.01% by vol. of TFA: CH₃CN+0.01% by vol. of TFA)); wavelength 220 nm; retention time: 3.33 min) and by mass spectroscopy (ESI-MS: M+1=618).

which is measured via an enzymatic regeneration of the product ADP to ATP by means of pyruvate kinase (PK) and subsequent coupling to an NADH-dependent lactate dehydrogenase (LDH) reaction. The reaction can be monitored via the change in absorbance at 340 nm by coupling to the NADH-dependent LDH. The regeneration of the ATP simultaneously ensures that the substrate concentration remains constant.

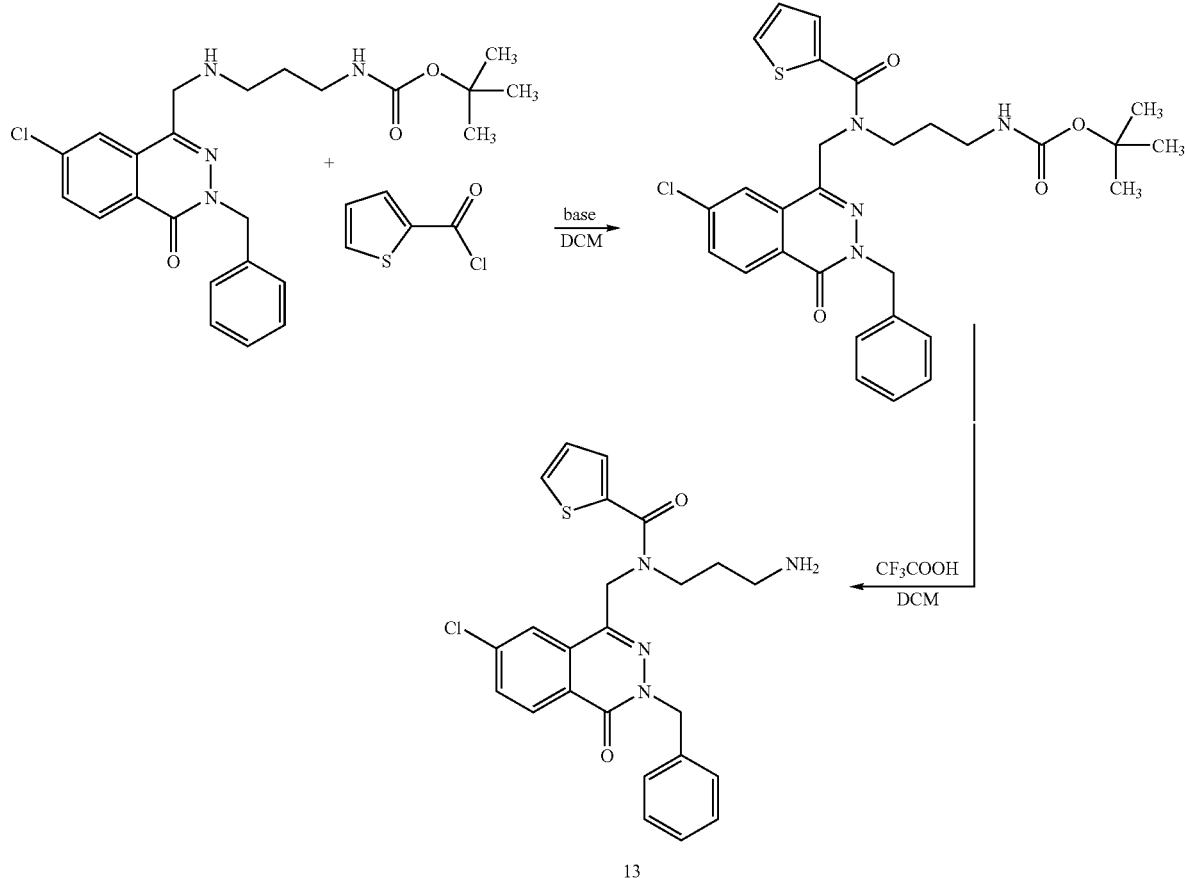

Compound 13 obtained in accordance with the above reaction scheme can be characterised by HPLC chromatography (column: Chromolith SpeedROD RP18e 50-4.6; gradient 5.5 min./flow rate: 2.75 ml (90:10-0:100 (H₂O+0.01% by vol. of TFA: CH₃CN+0.01% by vol. of TFA)); wavelength 220 nm; retention time: 1.93 min) and by mass spectroscopy (ESI-MS: M+1=467).

The characterisation of the compounds according to the invention obtained in accordance with the above examples can preferably additionally be confirmed by correlating $^1$H- and/or $^{13}$C-NMR spectroscopic data.

Example A

Assay I

The efficacy of the compounds according to the invention can be determined, for example, via the Eg5 ATPase activity, The changes in absorbance per time unit are analysed graphically and a linear regression carried out in the visually linear region of the reaction.

Example B

Assay II

The combination of the antiprotozoic pentamidine and the inhibitors of kinesin ATPase Eg5/KSP results in increased inhibitory effects in cell proliferation tests with the colon carcinoma cell line HCT116.

Eg5 inhibitors adversely affect the ATPase activity and inhibit the course of the cell cycle owing to an error in the separation of the spindle poles.

The determination of the efficacy of the compounds of the formula I according to the invention in combination with compounds of the formula VI and/or medicaments from Table I can be demonstrated as follows in combination assays:

$10^3$ to $10^4$ cells of a defined cell line (HCT116, Colo 205, MDA-MB 231, etc.) are sown into each well of a 96-well microtitre plate and cultivated overnight under standard conditions. For the substances of the combination to be tested, 10-50 mM stock solutions in DMSO were prepared. Dilution series (generally 3-fold dilution steps) of the individual substances were combined with one another in the form of a pipetting scheme (see scheme below), while maintaining a DMSO final concentration of 0.5% (v/v). Next morning, the substance mixtures were added to the cells, which were incubated under culture conditions for a further 48 hours. At the end of the cultivation, Crystal Violet staining of the cells was carried out. After extraction of the Crystal Violet from the fixed cells, the absorption at 550 nm was measured spectrophotometrically. It can be used as a quantitative measure of the adherent cells present.

melted, poured into moulds and allowed to cool. Each suppository contains 20 mg of active ingredient.

Example E

Solution

A solution is prepared from 1 g of an active ingredient of the formula 1, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Scheme

Compounds of the formula I

|   | 1 | 2 | 3 | 4 | 5 | 6 | 7 | 8 | 9 | 10 | 11 | 12 |
|---|---|---|---|---|---|---|---|---|---|----|----|----|
| A |   | 81 y | 27 y | 9 y | 3 y | y | 0 |   |   |    |    |    |
| B | 81 x |   |   |   |   |   |   |   | empty | empty | empty |    |
| C | 27 x |   |   |   |   |   |   |   | 0.5% DMSO | 0.5% DMSO | 0.5% DMSO |    |
| D | 9 x |   |   |   |   |   |   |   |   |    |    |    |
| E | 3 x |   |   |   |   |   |   |   |   |    |    |    |
| F | x |   |   |   |   |   |   |   |   |    |    |    |
| G | 0 |   |   |   |   |   |   |   |   |    |    |    |
| H |   |   |   |   |   |   |   |   |   |    |    |    |

Compounds of the formula VI

The following examples relate to medicaments:

Example C

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example D

Suppositories

A mixture of 20 g of an active ingredient of the formula I with 100 g of soya lecithin and 1400 g of cocoa butter is

Example F

Ointment 500 mg of an active ingredient of the formula I are mixed with 99.5 g of Vaseline under aseptic conditions.

Example G

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example H

Dragees

Tablets are pressed analogously to Example E and subsequently coated in a conventional manner with a coating of sucrose, potato starch, talc, tragacanth and dye.

Example I

Capsules 2 kg of active ingredient of the formula I are introduced into hard gelatine capsules in a conventional manner in such a way that each capsule contains 20 mg of the active ingredient.

Example J

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound or compounds of formula I

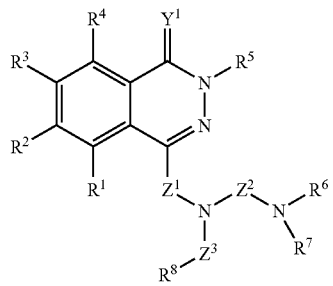

in which
R$^1$, R$^2$, R$^3$ and R$^4$, independently of one another, are H, A, Ar, Het, OR$^a$, SR$^a$, OAr, SAr, N(R$^a$)$_2$, N R$^a$Ar, Hal, NO$_2$, CN, (CH$_2$)$_m$COOR$^a$, (CH$_2$)$_m$COOAr, (CH$_2$)$_m$CON(R$^a$)$_2$, (CH$_2$)$_m$CONHAr, COR$^a$, COAr, S(O)$_m$A, S(O)$_m$Ar, NHCOA, NHCOAr, NHSO$_2$A, NHSO$_2$Ar or SO$_2$N(R$^a$)$_2$,
R$^a$ is H, A, Ar, Het, aralkyl or heteroaralkyl,
R$^5$, R$^8$, independently of one another, are H, A, Ar, Het, aralkyl or heteroaralkyl, and
R$^6$, R$^7$, independently of one another, are H or A, or, together with the N atom to which they are bonded, form a saturated or unsaturated 5-, 6- or 7-membered heterocycle, which heterocycle optionally contains 1, 2 or 3 further heteroatoms selected from the group consisting of N, S and O,
Y$^1$ is O, S or NR$^1$,
Z$^1$, Z$^2$, Z$^3$, independently of one another, are (CR$^9$R$^{10}$)$_n$ or (CR$^9$R$^{10}$)$_p$—(C=Y$^2$)—(CR$^{11}$R$^{12}$)$_q$,
A is alkyl or cycloalkyl,
Ar is aryl or heteroaryl,
Het is heteroaryl or heterocyclyl,
Hal is F, Cl, Br or I,
Y$^2$ is O, S or NR$^2$,
R$^9$, R$^{10}$, R$^{11}$, R$^{12}$, independently of one another, are H, A, OA, Ar, Het, aralkyl or heteroaralkyl,
m is 0, 1, 2 or 3,
n is 1, 2, 3 or 4, and
p, q, independently of one another, are 0, 1, 2 or 3, or physiologically acceptable, tautomers, salts or stereoisomers of said compound or compounds of formula I or mixtures thereof in all ratios.

2. The compound or compounds according to claim 1, selected from a compound or compounds of formula I'

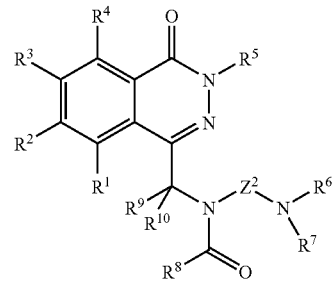

in which
R$^9$, R$^{10}$, independently of one another, are selected from the group consisting of H, A, OA, Ar, Het, aralkyl and heteroaralkyl.

3. The compound or compounds according to claim 1 in which
R$^1$ and R$^4$ independently of one another, either are H or are selected from the group consisting of A, CF$_3$, OCF$_3$, OR$^a$, SA, S(O)$_2$A, S(O)A, CH$_2$CN, COOA, CONHA, Hal, SCF, CN and Het.

4. The compound or compounds according to claim 1 in which
R$^3$ and R$^4$, independently of one another, are selected from the group consisting of H and Cl.

5. The compound or compounds according to claim 1 in which
R$^5$ is selected from the group consisting of Ar, aralkyl and heteroaralkyl,
R$^6$, R$^7$, independently of one another, are selected from the group consisting of H, A, Ar and aralkyl, and
R$^8$ is selected from the group consisting of A, Ar and Het.

6. The compound or compounds according to claim 1 in which
R$^5$ is unsubstituted or substituted benzyl, and
R$^8$ is unsubstituted or substituted phenyl.

7. The compound or compounds according to claim 1, selected from the group consisting of sub-formulae IA to IP:

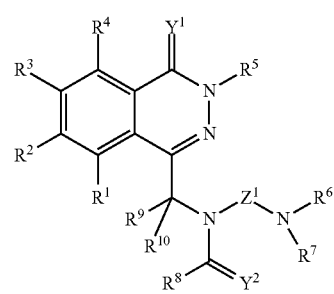

-continued
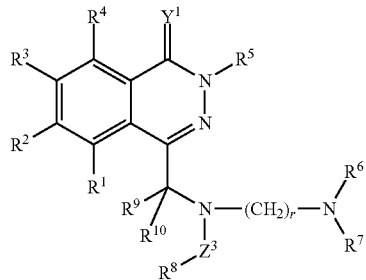
IB
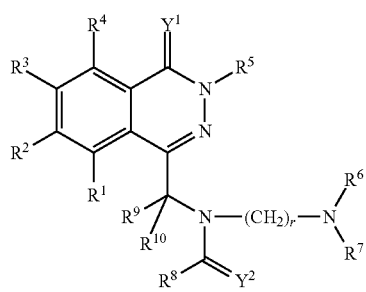
IC
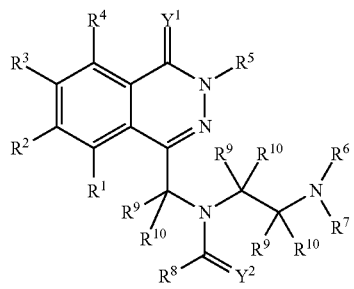
ID
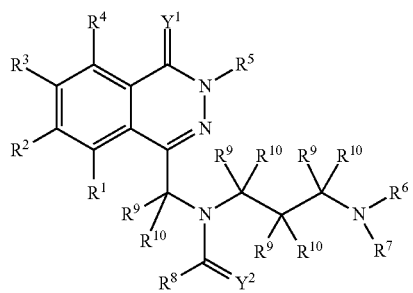
IE
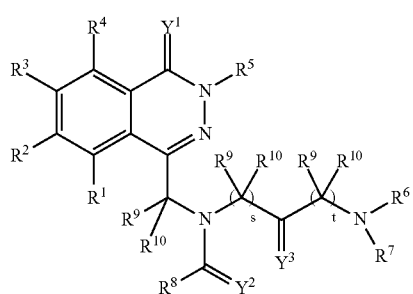
IF
-continued
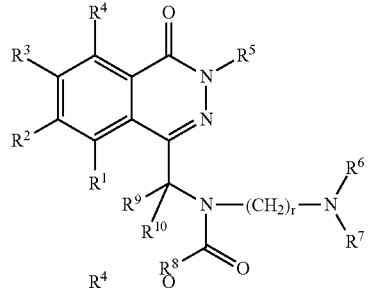
IG
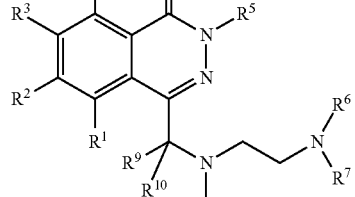
IH
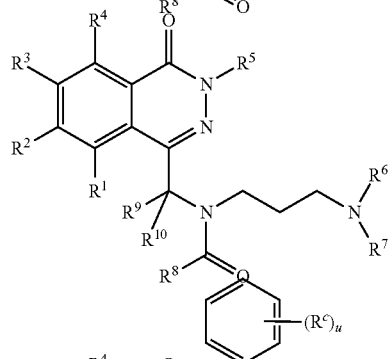
Ii
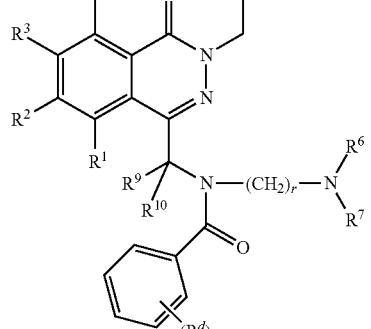
IJ
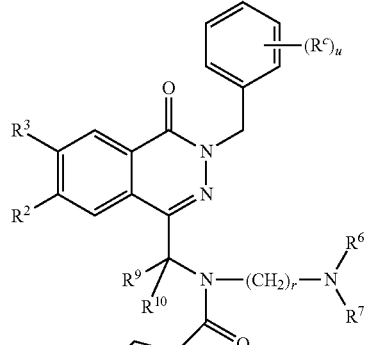
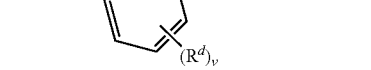
IK IL 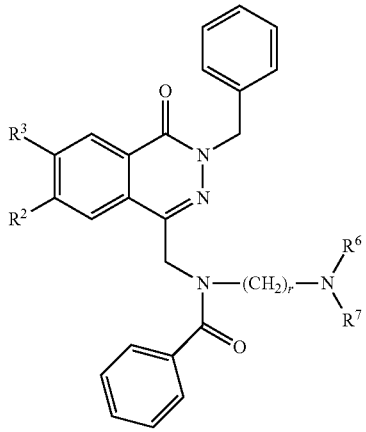

IM 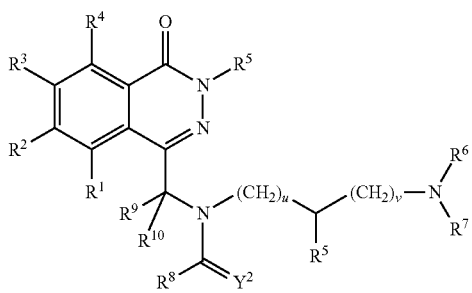

IN 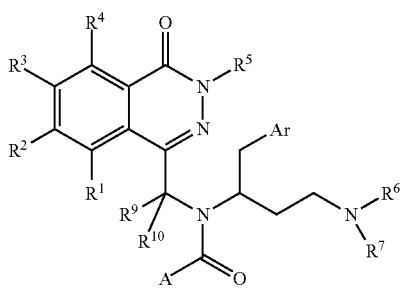

IO 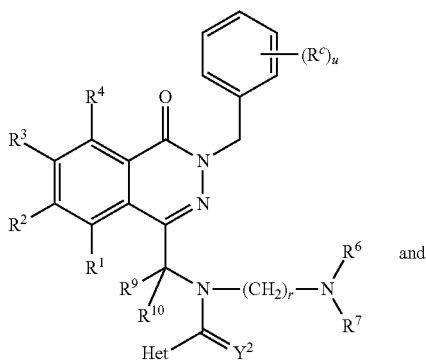

and

IP 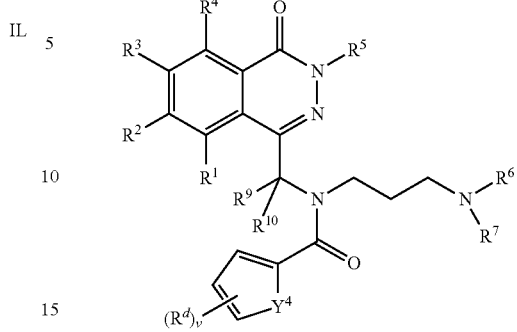

in which $R^1$, $R^2$, $R^3$, $R^4$, $R^5$, $R^6$, $R^7$, $R^8$, $R^9$, $R^{10}$, $Y^1$, $Y^2$, $Z^1$ and $Z^3$ have the meanings indicated in claim 1, r is 1, 2, 3 or 4, s and t, independently of one another, are 0, 1 or 2, $Y^3$ is O, S or $NR^2$, $Y^4$ is O, S or $NR^a$, in which $R^a$ has the meaning indicated in claim 1, A is alkyl, Ar is aryl or heteroaryl, Het is heteroaryl, $R^c$ and $R^d$, independently of one another, are selected from the meanings indicated for $R^1$ to $R^4$, and u and v, independently of one another, are 0, 1, 2 or 3, physiologically acceptable, tautomers, salts or stereoisomers thereof and mixtures thereof in all ratios.

8. The compound or compounds according to claim 1, selected from the group consisting of:

N-(3-benzyl-7-chloro-4-oxo-3,4-dihydrophthalazin-1-yl-methyl)-N-(3-di-methylaminopropyl)benzamide;

N-(3-benzyl-7-chloro-4-oxo-3,4-dihydrophthalazin-1-yl-methyl)-N-(2-di-methylaminoethyl)benzamide;

N-(2-aminoethyl)-N-(3-benzyl-7-chloro-4-oxo-3,4-dihydrophthalazin-1-ylmethyl)benzamide;

N-(3-aminopropyl)-N-(3-benzyl-7-chloro-4-oxo-3,4-di-hydrophthalazin-1-yl-methyl)benzamide;

N-(3-aminopropyl)-(3-benzyl-7-chloro-4-oxo-3,4-dihy-drophthalazin-1-ylmethyl)thiophene-2-carboxamide;

N-(3-amino-1-benzylpropyl)-N-(3-benzyl-7-chloro-4-oxo-3,4-dihydrophthalazin-1-ylmethyl)isobutyramide;

physiologically tolerated, salts, tautomers, stereoisomers and mixtures thereof in all ratios.

9. A method for the preparation of the compound or compounds of the formula I according to claim 1, comprising:

a) a compound or compounds of the formula II

II 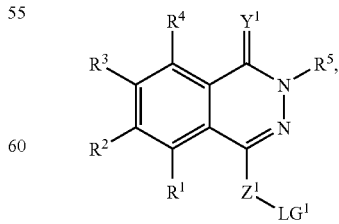

in which $R^1$, $R^2$, $R^3$, $R^4$, $R^5$, $Y^1$ and $Z^1$ have the meanings indicated in claim 1, and $LG^1$ is a leaving group, is reacted with a compound or compounds of the formula III

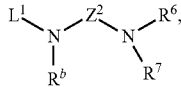   III in which
$R^6$, $R^7$ and $Z^2$ have the meanings indicated in claim 1,
$L^1$ is H or a metal atom,
$R^b$ is $L^2$ or $Z^3$—$R^8$, in which
$L^2$ is H or a metal atom, and
$Z^3$ and $R^8$ have the meanings indicated in claim 1,
and, if $R^b$ is $L^2$, the product of the formula IV

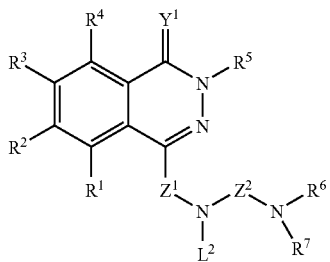   IV obtained in reaction step a) is
b) reacted with a compound or compounds of the formula V

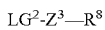   V, in which
$Z^3$ and $R^8$ have the meanings indicated in claim 1, and
$LG^2$ is a leaving group,
and optionally
c) the resultant compound or compounds of the formula I is isolated and/or treated with an acid or a base in order to convert it into one of its salts.

10. A compound or compounds of the formula II

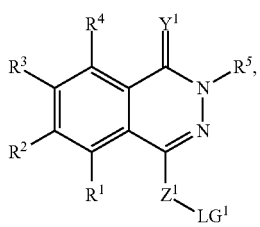   II in which $R^1$, $R^2$, $R^3$, $R^4$, $R^5$, $Y^1$ and $Z^1$ have the meanings indicated in claim 1, and $LG^1$ is a leaving group, or physiologically acceptable salts, tautomers or stereoisomers thereof or mixtures thereof in all ratios.

11. A medicament or medicaments comprising at least one compound according to claim 1 in a pharmaceutical formulation and further optionally comprising excipients and/or adjuvants.

12. A mixture comprising one or more compounds of claim 1 and an amount of one or more compound or compounds of the formula VI,

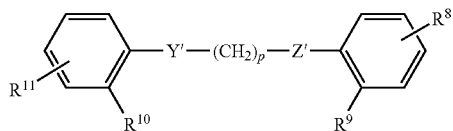   VI in which
Y' and Z' each, independently of one another, are O or N,
$R^9$ and $R^{10}$ each, independently of one another, are H, OH, halogen, O-alkyl, $OCF_3$, $NO_2$ or $NH_2$,
p is 2, 3, 4, 5, or 6, and
$R^8$ and $R^{11}$ are each, independently of one another, in the meta- or para-position in relation to $Y^1$, $Z^1$, $R^9$, or $R^{10}$, and are selected from the group consisting of:

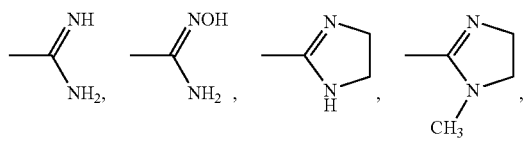

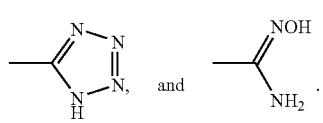

13. The mixture of claim 12, wherein the compound or compounds of the formula VI is pentamidine or salts thereof.

* * * * *